(12) United States Patent
Parris et al.

(10) Patent No.: US 7,604,593 B2
(45) Date of Patent: Oct. 20, 2009

(54) METHODS FOR MEASURING ANALYTE IN A SUBJECT AND/OR COMPENSATING FOR INCOMPLETE REACTION INVOLVING DETECTION OF THE ANALYTE

(75) Inventors: Norman A. Parris, Belmont, CA (US); Russell O. Potts, San Francisco, CA (US); Michael J. Tierney, San Jose, CA (US); Christopher Uhegbu, San Leandro, CA (US)

(73) Assignee: Animas Corporation, West Chester, PA (US)

( * ) Notice: Subject to any disclaimer, the term of this patent is extended or adjusted under 35 U.S.C. 154(b) by 940 days.

(21) Appl. No.: 11/042,865

(22) Filed: Jan. 24, 2005

(65) Prior Publication Data
US 2005/0130249 A1    Jun. 16, 2005

Related U.S. Application Data

(62) Division of application No. 09/859,218, filed on May 14, 2001, now Pat. No. 6,885,883.

(60) Provisional application No. 60/204,397, filed on May 16, 2000, provisional application No. 60/244,078, filed on Oct. 27, 2000.

(51) Int. Cl.
*C12Q 1/54* (2006.01)
*A61B 5/05* (2006.01)
*A61B 5/00* (2006.01)

(52) U.S. Cl. .................. 600/365; 600/345; 600/347; 435/14

(58) Field of Classification Search ............. 600/347, 600/365; 435/14
See application file for complete search history.

(56) References Cited

U.S. PATENT DOCUMENTS

| 5,279,543 A | 1/1994 | Glikfeld et al. |
| 5,362,307 A | 11/1994 | Guy et al. |
| 5,636,632 A | 6/1997 | Bommannan et al. |
| 5,730,714 A | 3/1998 | Guy et al. |
| 5,735,273 A | 4/1998 | Kurnik et al. |
| 5,771,890 A | 6/1998 | Tamada |

(Continued)

FOREIGN PATENT DOCUMENTS

WO    WO 99/29230    6/1999

(Continued)

OTHER PUBLICATIONS

Bacon et al., "Predictive, Error-Compensating Kinetic Method for Enzymatic Quantification of Creatinine in Serum," *Clin Chem.* 37(8):1338-1344 (1991).

(Continued)

*Primary Examiner*—Patricia C Mallari

(57) ABSTRACT

The present invention relates to a predictive-kinetic method for use with data processing of a sensor-generated signal, as well as, microprocessors and monitoring systems employing such a predictive-kinetic method. Data from a transient region of a signal is used with suitable models and curve-fitting methods to predict the signal that would be measured for the system at the completion of the reaction. The values resulting from data processing of sensor response using the methods of the present invention are less sensitive to measurement variables.

19 Claims, 19 Drawing Sheets

U.S. PATENT DOCUMENTS

| | | | |
|---|---|---|---|
| 5,827,183 | A | 10/1998 | Kurnik et al. |
| 5,954,685 | A | 9/1999 | Tierney |
| 5,989,409 | A | 11/1999 | Kurnik et al. |
| 5,995,860 | A | 11/1999 | Sun et al. |
| 6,023,629 | A | 2/2000 | Tamada |
| 6,201,979 | B1 | 3/2001 | Kurnik et al. |
| 6,272,364 | B1 * | 8/2001 | Kurnik .................. 600/345 |

FOREIGN PATENT DOCUMENTS

| | | |
|---|---|---|
| WO | WO 99/58050 | 11/1999 |
| WO | WO 01/88534 | 11/2001 |

OTHER PUBLICATIONS

Bacon et al., "Kinetic Study of the Jaffe Reaction for Quantifying Creatinine in Serum: 2. Evaluation of Buffered Reagent and Comparison of Different Date-Processing Options," *Clin Chem.* 35(3):360-363 (1989).

Chen et al., "Evaluation of Alternative Measurement and Data-Processing Options for Enzyme-Based Biosensors," *Analytica Chimica Acta* 388:231-241 (1999).

Engh et al., "Improvement of Reaction Rate Measurement Precisions Using the Temproally Optimized Fixed-Time Ratemeter," *Anal. Chem.* 60:p. 545 (1988).

Gondo et al., "Studies on Dynamic Behavior of the Biosensor Based on Immobilized Glucoamylase-glucose Oxidase Membrane," *Biosens. Bioelectron* 12(5):395-401 (1997).

Harris, R.C., "Kinetic Methods That are Independent of the Rate of Reaction," *Clin. Chem* 29: p. 2079 (1983).

Ho, M.H., "Kinetic Methods That are Independent of the Rate of Reaction," *Biomed. Sci. Instrum.* 20:85-91 (1984).

Kaku et al., "Amperometric Glucose Sensors Based on Immobilized Glucose Oxidase-Polyquinone System," *Anal. Chem.* 66(8):1231-1235 (1994).

Karube et al., "Integrated Microbiosensors for Medical Use," *Ann. N.Y. Acad. Sci* 542:470-479 (1988).

Lin et al., "Error-Compensating Kinetic Method for Enzymatic Determination of DNAs," *Clin. Chem.* 28(10):2081-2807 (1982).

Lin et al., "Multipoint Kinetic Methods Evaluated for Quantitation of Theophylline with Prosthetic Group Label Immunoassay," *Clin. Chem.* 39(9):1850-1856 (1993).

Linke et al., "Prevention of the Decrease in Sensitivity of an Amperometric Glucose," *Clin. Chem.* 45(2):283-285 (1999).

Love et al., "Evaluation of Transient Responses of Ammonia-Selective Potentiometric Electrodes for Quantitative Applications," *Analytical Chemistry* 64(11):1269-1276 (1992).

Malitesta et al., "Glucose Fast-Response Amperometric Sensor Based on Glucose Oxidase Immobilized in an Electropolymerized Poly (o-phenylenediamine) Film," *Anal. Chem.* 62(24):2735-2740 (1990).

Meiling et al., "Kinetic Method That is Insensitive to Variables Affecting Rate Constants," *Anal. Chem.* 50:p. 1611 (1978).

Meiling et al., "A Kinetic for Glucose That is Insensitive to Variations in Temperature and Enzyme Activity," *Clinical Chemistry* 25(9):1581-1590 (1979).

Pardue, H. L., "Kinetic Aspects of Analytical Chemistry," *Anal. Chim. Acta* 69:216 (1989).

Pardue et al., "Evaluation of a Discrete Sampler/Stopped-Flow Mixer System for Equilibrium and Kenetic Analyses," *Clinical Chemistry* 23(7):1230-1237 (1977).

Pardue, H.L., "Unified View of Kinetic-Based Analytical Methods with Emphasis on Ruggedness," *The Analyst* 121:385-390 (1996).

Przybyt, M., "Influence of Anions on Glucose Electrode Response: Application to Extending Concentration Range," *Biosensors & Bioelectronics* 13(3-4):471-477 (1998).

Rinken et al., "Calibration of Glucose Biosensors by Using Pre-Steady State Kinetic Data," *Biosensors & Bioelectronics* 13(7-8):801-807 (1998).

Tang et al., "Optimisation of Enzyme Electrodes," *Med. Biol. Eng. Comput.* 28(3):B18-24 (1990).

Tse et al., "Transient Response of an Enzyme Electrode Sensor for Glucose," *Anal. Chem.* 59(19):2339-2344 (1987).

Uhegbu, et al., "Initial Studies of a New Approach to the Design and Use of Enzyme-Based Reactor/Sensor Systems: Amperometric System for Glucose," *Anal. Chem.* 65(18):2443-2451 (1993).

Uhegbu et al., "Management of Interferences in a Transdermal, Noninvasive Glucose Monitoring Device," *Clinical Chemistry* 45(9):1679-1681 (1999).

Uhegbu, et al., "Data-Processing Method to reduce error Coefficients for Membrane-Based Analytical Systems. 1. Ampereometric-Based Sensor Evaluated for Quantification of Oxygen," *Anal. Chem.* 64(20):2378-2382 (1992).

Wentzell et al., "Reaction-Rate Method of Analysis Insensitive to Between-Run Changes in Rate Constant," *Anal. Chem.* 58:p. 851(1986).

Willis, et al., "Simultaneous Kinetic Determination of Mixtures by On-Line Regression Analysis," Analytical Chemistry 42(12):1350-1355 (Oct. 1970).

Wollenberger, U., "Electrochemical Biosensors—Ways to Improve Sensor Performance," *Biotechnology Genetic Engineering Reviews* 13:237-266 (1996).

Yokoyama, K., "Mediated Microbiosensors," *Applied Biochemistry Biotechnology Appl. Biochem. Biotechnol.* 41(1-2):17-18 (1993).

Xu, L., et al., "Optimization Method for Simultaneous Kinetic Analysis," Analytical Chemistry 68(11):1842-1850 (Jun. 1996).

* cited by examiner

| MODEL NAME | MODEL EQUATION |
|---|---|
| First-order | $S_t = S_\infty - (S_\infty - S_0)e^{-kt}$ |
| Second-order | $S_t = S_\infty - 1/[1/(S_\infty - S_0) \pm k_2 t]$ |
| Variable-order | $S_t = S_\infty \mp \{k_s(n-1)t + [\pm(S_\infty - S_0)]^{1-n}\}^{1/(1-n)}$ |
| Parallel first-order | $S_t = S_0 + S_{\infty 1}(1-e^{-k_1 t}) + S_{\infty 2}(1-e^{-k_2 t})$ |
| Hyperbolic and first-order | $S_t = S_0 + (S_{\infty h} - S_0)t/(\tau + t) + S_{\infty f}(1-e^{-k_1 t})$ |
| Hyperbolic | $S_t = S_0 + (S_\infty - S_0)t/(\tau + t)$ |
| Linear Müller | $t/S_t = \tau/S_\infty + t/S_\infty$ |
| Massart | $S_t = S_\infty - (S_\infty - S_0)e^{-t/\tau}/(1 + \alpha t)$ |
| Buck | $S_t = S_0 + \ln\{e^{(S_\infty - S_0)f} - [e^{(S_\infty - S_0)f} - 1]e^{-kt}\}$ |
| One Point Fixed Time | $S_t = bS_\infty$ |
| First and zero-order | $S_t = S_\infty - (S_\infty - S_0)e^{-k_1 t} + k_0 t$ |
| First and zero-order with quadratic term | $S_t = S_\infty - (S_\infty - S_0)e^{-k_1 t} + k_0 t + k_2 t^2$ |
| First-order and square root | $S_t = S_0 - (S_\infty - S_0)e^{-k_1 t} + bt^{1/2}$ |
| First-order and square root with time shift | $S_t = S_0 - (S_\infty - S_0)e^{-k_1 t} + b(t - t_0)^{1/2}$ |
| Michaelis-Menten | $dS/dt = V_{max}(S_\infty - S_t)/[K_m + (S_\infty - S_t)/(eb)]$ |
| Flux model | $S_t = S_0 + (S_\infty - S_0)\{1 + 2\sum_{i=0}^{\infty}(-1)^i \exp(-ki^2\pi^2 t)\}$ |
| Flux model with time shift | $S_t = S_0 + (S_\infty - S_0)\{1 + 2\sum_{i=0}^{\infty}(-1)^i \exp[-ki^2\pi^2(t - t_0)]\}$ |

*FIG. 13*

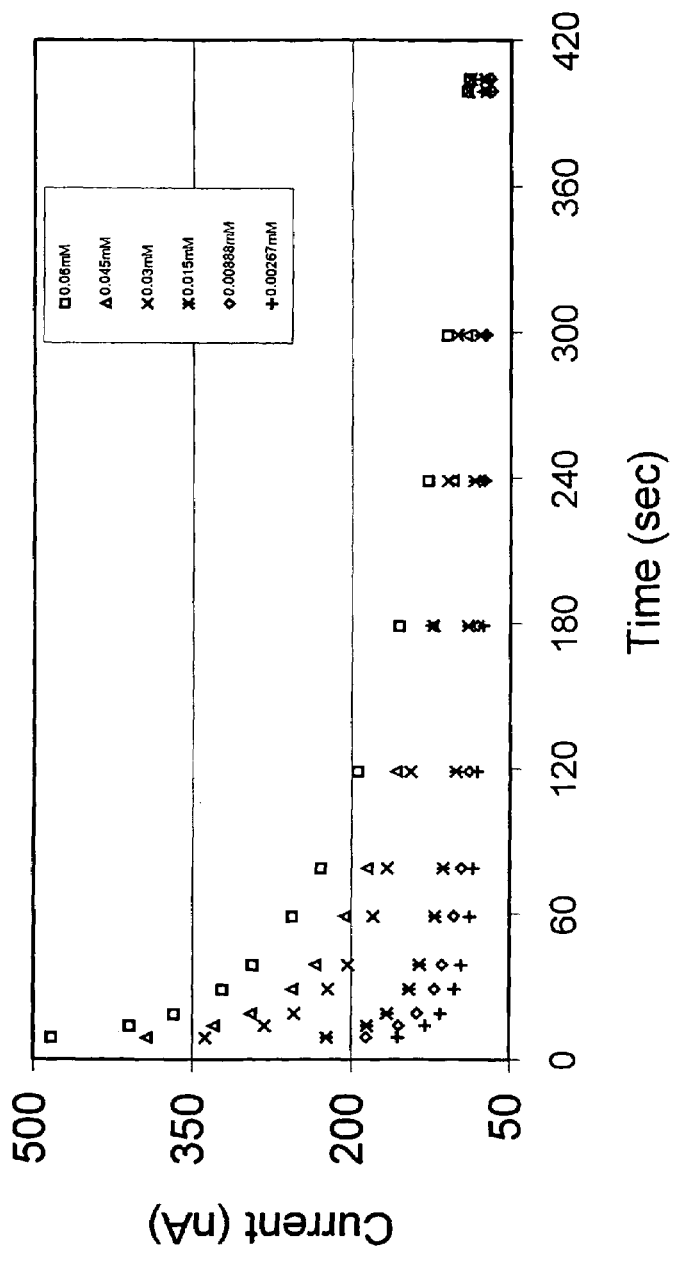

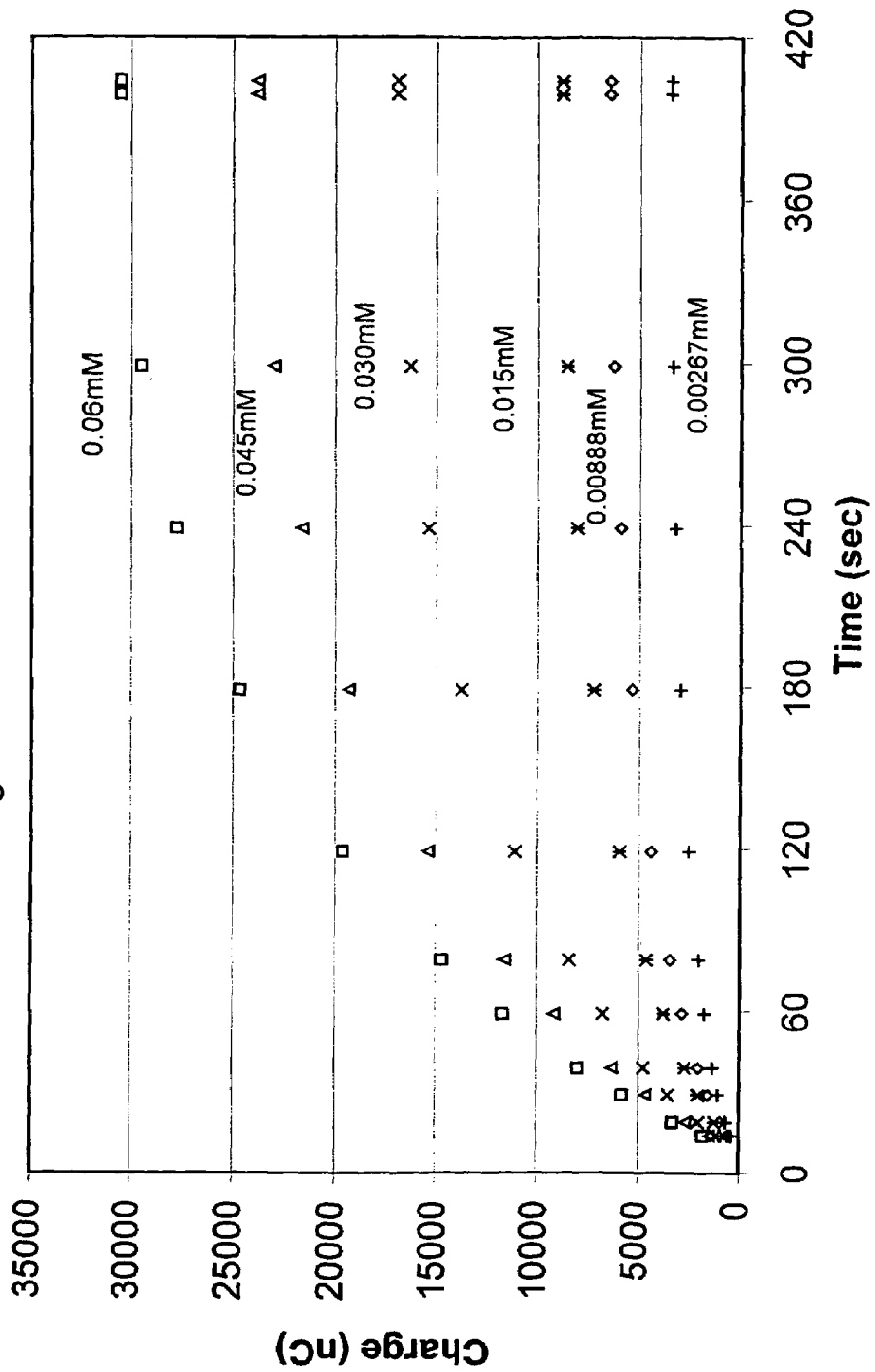

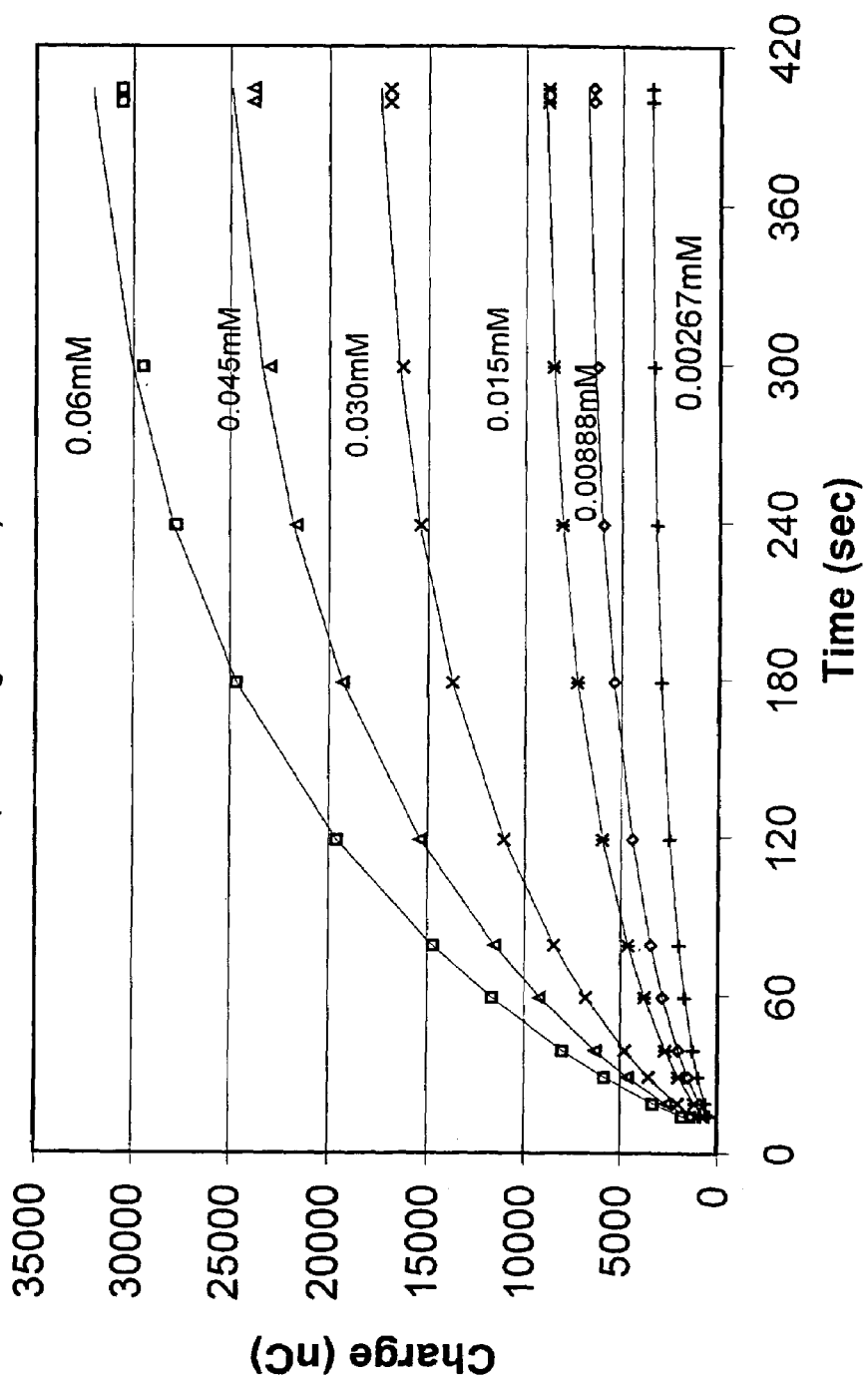
Figure 16: Fitted and Bkgrd Corrected Experimental Data (Fit Range: 3mins)

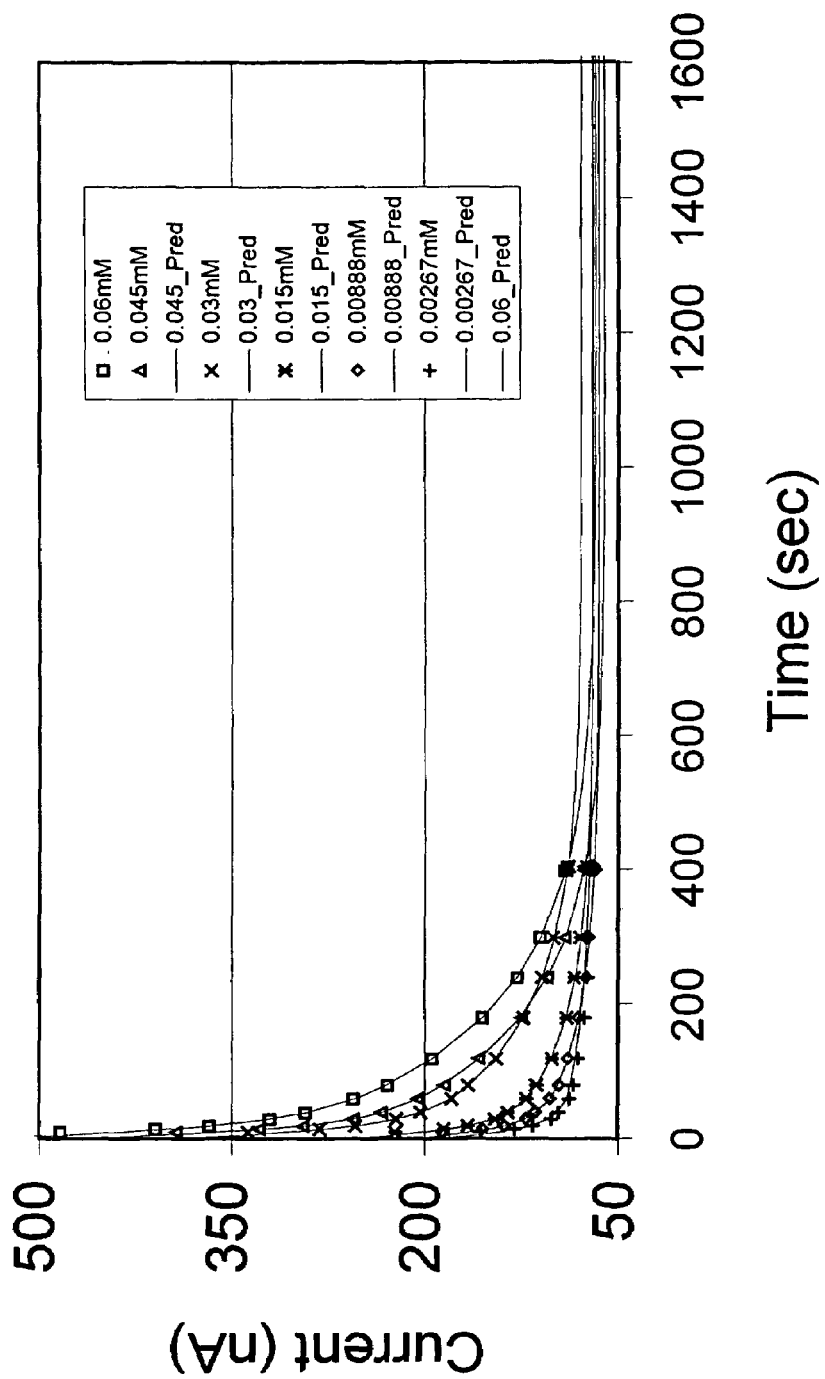

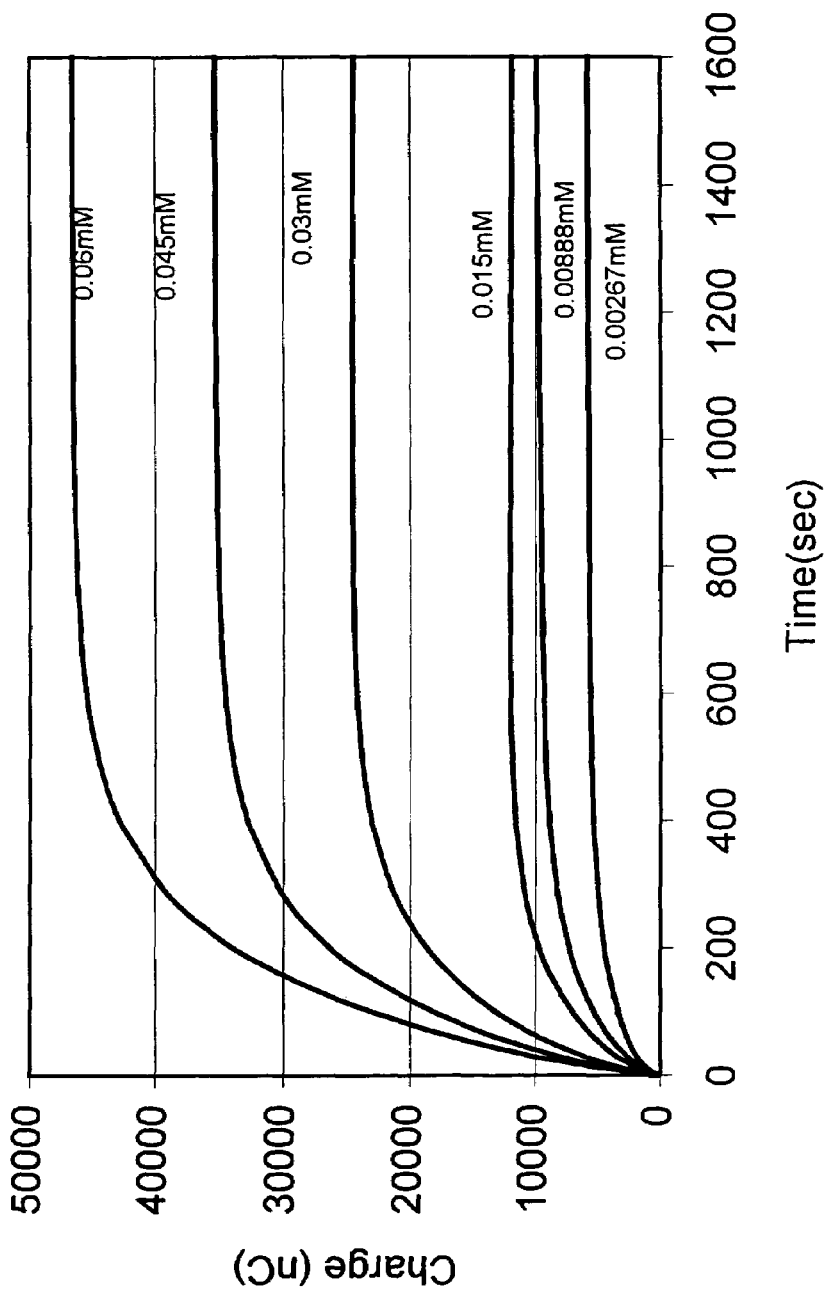
Figure 18: Integrated Responses from Predicted Current Signal after Correction using Predicted Bkgrd Signal (Fit range: 30-405secs)

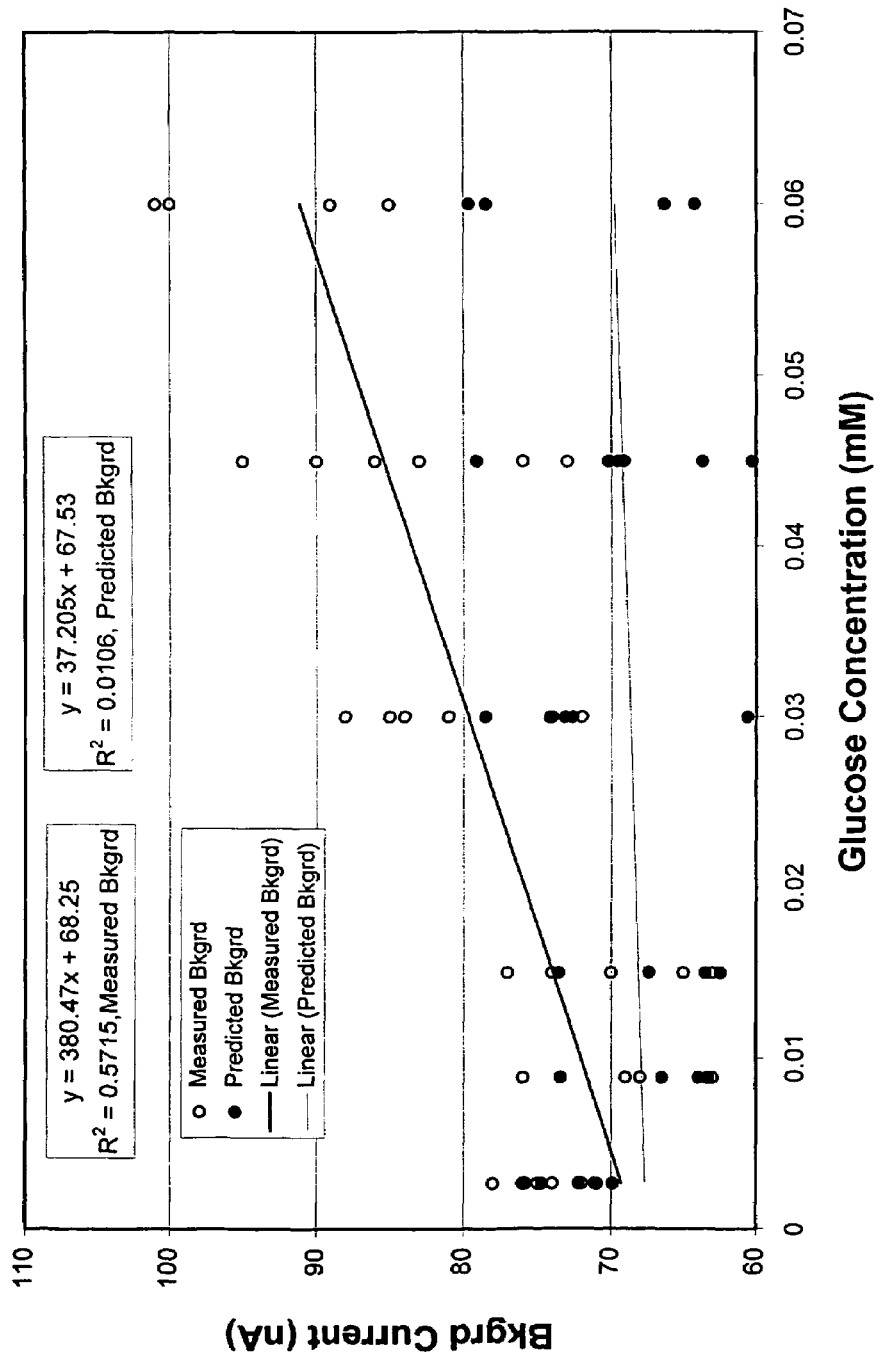

METHODS FOR MEASURING ANALYTE IN A SUBJECT AND/OR COMPENSATING FOR INCOMPLETE REACTION INVOLVING DETECTION OF THE ANALYTE

CROSS-REFERENCE TO RELATED APPLICATIONS

This application is a divisional of U.S. Patent Application Ser. No. 09/859,218, filed 14 May 2001, now U.S. Pat. No. 6,885,883 now allowed, which claims the benefit of U.S. Provisional Application Ser. Nos. 60/204,397, filed 16 May 2000, and 60/244,078, filed 27 Oct. 2000, all which applications are incorporated herein by reference in their entireties.

TECHNICAL FIELD

The present invention relates generally to the use of a predictive-kinetic method to reduce the effects of measurement variables on results obtained using analyte sensors. The invention includes a method and device for measuring the concentration of target analytes present in a biological system, for example, a mammalian subject. More particularly, the invention relates to methods, microprocessors, and monitoring systems for predicting an amount or concentration of an analyte using a series of measurements obtained from a monitoring system and employing a predictive-kinetic algorithm.

BACKGROUND OF THE INVENTION

Measurement and data-processing approaches related to enzyme reaction-based biosensors have historically been based on evaluation of non-equilibrium steady-state responses. Two limitations of such analyses include the following: (i) loss of sensitivity as the substrate concentration approaches and exceeds the corresponding Michaelis constant of the enzyme immobilized on the sensor, and (ii) adverse influences on measured values due to changes in experimental variables that influence (a) rates of chemical reactions, and (b) physical processes that control the steady state response.

Similar problems have been encountered in conventional kinetic-based methods when they are applied to enzymatic determinations of analytes in homogeneous solutions (Chen, W., et al., Analytica Chimica Acta 388:231-241, 1999). Results of such analyses generally have limited ranges of linearity and are influenced by experimental variables that affect enzyme activity. Steady-state data-analysis methods applied to enzyme reaction-based sensors are influenced by variables that affect rates of reaction and rates of mass transport. However, application of initial-rate methods using enzymes in homogenous solution (i.e., kinetic-based solution methods) tend to be influenced only by variables that affect rates of reactions provided the solutions are well-stirred.

A variety of measurement and data-processing approaches have been used in attempts to reduce or eliminate problems in homogenous solution measurement of analyte concentrations including, but not limited to, the following. Engh, et al., (Anal. Chem. 60:545, 1988), used alternative applications of a rate-based approach and showed improvement in the ruggedness of enzymatic methods but also demonstrated that the methods did little to improve the sensitivity at high concentrations of substrate. For homogenous solution analyses, a two-rate method (Wentzell, P. D., et al, Anal. Chem. 58:2851, 1986) and pseudoequilibrium methods (Meiling, G. E., et al., Anal. Chem. 50:1611, 1978; Harris, R. C., Clin. Chem. 29:2079, 1983) have demonstrated the potential to reduce dependencies on experimental variables to a similar degree as has been seen with equilibrium methods. Further, the two-rate and pseudoequilibrium methods, when used in this way, appear to maintain high sensitivity for analyte concentrations above Michaelis constants.

Two-rate and pseudoequilibrium methods (based on homogenous system methods) have been applied to enzyme-based biosensor methods to determine if these methods could be adapted to biosensors such that measurement improvements would be seen which were similar to those achieved in homogenous solution (Chen, et al., Analytica Chimica Acta 388:231-241, 1999; Wentzell, P. D., et al, Anal. Chem. 58:2851, 1986; Meiling, G. E., et al., Anal. Chem. 50:1611, 1978; Harris, R. C., Clin. Chem. 29:2079, 1983). The enzyme-based biosensor typically used in such studies consisted of an enzyme and an electron mediator immobilized on the surface of a glassy-carbon electrode (e.g., Chen, et al., Analytica Chimica Acta 388:231-241, 1999). Although some improvements in performance characteristics of the enzyme-based biosensor were observed, both methods were shown to have limitations when applied to enzyme-based biosensor data.

SUMMARY OF THE INVENTION

The present invention relates to methods, microprocessors, and monitoring systems for predicting a concentration or amount of an analyte using measurements obtained from a monitoring system and employing a predictive-kinetic algorithm. In one embodiment, the present invention relates to a method for measuring the amount or concentration of an analyte present in a biological system. In the method, a sample comprising the analyte of interest is transdermally extracted using a sampling system, for example, by ionotophoresis, sonophoresis, laser-formed micro-holes and suction, where the sampling system is in operative contact with a skin or mucosal surface of the biological system. Typically, frequent samples are obtained over time while the sampling system remains in operative contact with the surface. A measured signal is obtained, e.g., employing a sensing device, from the extracted analyte. Typically the measured signal is a response curve comprising data points with respect to time. The measured signal is specifically related to the amount or concentration of analyte, and the response curve comprises kinetic and equilibrium regions. At least one mathematical model comprising selected parameters is chosen where the model describes the curve. In preferred embodiments, the mathematical model is selected from the group consisting of a first order process, combined first order and zero order process, a parallel multiple first order process, a flux process, an nth order process (where n does not equal one), and mixtures and combinations thereof.

The model and an error minimization method are iteratively used to provide a predicted response curve corresponding to the measured signal response curve, wherein (i) the error minimization method provides a calculated error (e.g., chi-square) based on differences between the predicted and measured signal response curves, and (ii) the estimating is iteratively performed until the calculated error between the predicted and measured signal response curves falls within an acceptable range or until no further statistically significant change is seen in the calculated error. At this point, iterative estimation of the parameters is stopped. The iterative estimation and error minimization results in a predicted response curve corresponding to the measured signal response curve. The predicted response curve yields a predicted end-point value and a measurement correlated to the amount or concentration of the analyte. For example, when the analyte sensor is detecting current, the end-point value obtained using the predictive-kinetic method typically represents a final background value. In one embodiment, the current is obtained from a system after introduction of the analyte (e.g., by transdermal extraction) and application of an appropriate potential. In a further example, after integration of a predicted response curve based on current, the end-point analyte-related value typically represents an area under the curve. A background correction step may be performed prior to integration, for example, the final background value obtained from the predicted current response curve may be employed for background subtraction, the predicted current response curve integrated and the end-point analyte-related value determined.

Exemplary embodiments of the measured signal are current and charge. The mathematical model may further comprise more than one process and each process may comprise selected parameters. In a further embodiment, each process may be associated with a weighting factor. In addition, the mathematical model may comprise a zero-order process, and/or at least one quadratic or square root term. Background subtraction may also be performed on the measured signal, for example, before application of the predictive-kinetic methods.

In some embodiments of the present invention, the end-point analyte-related value is converted to an amount or concentration of the analyte using, for example, a method comprising a calibration value (e.g., a ratio, a calibration point, a difference value, etc.).

Typically, at least two analyte samples are obtained and their corresponding measured signal response curves analyzed to provide a "series of measurements." In some embodiments of the present invention, conversion of the end-point or equilibrium analyte-related value to correspond to the amount or concentration of analyte can be carried on as each end-point analyte-related value is obtained, calculated together at the end, calculated in clusters, or any combination thereof.

In one aspect of the invention, at least three data points are obtained from the kinetic region of the curve, and these data points are used to estimate the half-life of the signal. The estimates of the half-life ($t_{1/2}$) may comprise, for example, estimating a rate constant (k) using a first order model. The obtaining of measured signal can then be carried out for a period of time determined based on the half-life, for example, the obtaining of measured signal can continue for a time period corresponding to at least three half-lives of the signal.

In an alternative embodiment, obtaining the measured signal can be carried out for a predetermined period of time. Such a defined time period may be, for example, empirically determined.

The measured signal may be transformed in a variety of ways before estimation of the end-point analyte-related values using the mathematical model, for example, the measured signal data can be integrated. Integration can be performed, for example, with or without background correction of the original signal (e.g., using background subtraction, see below). In one embodiment, background subtraction is performed by subtracting the predicted final background value from each point making up the predicted response. curve, the background corrected predicted response curve is then integrated to obtain an end-point analyte-related value.

For different measurements in a series (i.e., for different measured signal data curves obtained at different time points) different mathematical models may be selected to estimate the end-point values. Alternately, all end-point values may be estimated using a single mathematical model.

In one embodiment of the present invention, the mathematical model comprises a first order process, for example, the first order process may comprise the following:

$$S_t = S_\infty - (S_\infty - S_o)e^{-kt} \qquad \text{(Eqn. 1)}$$

where $S_o$, $S_t$, and $S_\infty$ are initial, intermediate, and end-point signals, k and t are the observed first-order rate constant and time, respectively.

In another embodiment of the present invention, the mathematical model comprises a parallel multiple first order process, for example, the parallel multiple first order process may comprise the following:

$$S_t = S_o + (S_{\infty 1} - S_o)*(1-e^{-k1t}) + (S_{\infty 2}-S_o)*(1-e^{-k2t}) + (S_{\infty 3}-S_o)*(1-e^{-k3t}) + \ldots \qquad \text{(Eqn. 6A)}$$

where $S_o$, $S_t$ are initial and intermediate signals, $S_{\infty 1}$, $S_{\infty 2}$, $S_{\infty 3}$, etc., are end-point signals (related to $k_1$, $k_2$, $k_3$, etc., respectively), $k_1$, $k_2$, $k_3$, etc., are the observed first-order rate constants, and t is time. In this embodiment, the predicted end-point value may be described by the following equation $$S_\infty = (S_{\infty 1} + S_{\infty 2} + S_{\infty 3} + \ldots) + S_o \qquad \text{(Eqn. 6B)}.$$

Further, a change in the predicted end-point value relative to the initial signal is described by the following equation:

$$\Delta S_\infty = (S_{\infty 1} + S_{\infty 2} + S_{\infty 3} + \ldots) \qquad \text{(Eqn. 6C)}.$$

The parallel multiple first order process may comprises the following:

$$S_t = S_o + (S_{\infty 1}-S_o)*(1-e^{-k1t}) + (S_{\infty 2}-S_o)*(1-e^{-k2t}) \qquad \text{(Eqn. 10)}$$

where $S_o$, and $S_t$, are initial and intermediate signals, $S_{\infty 1}$, and $S_{\infty 2}$ are end-point signals (related to $k_1$ and $k_2$, respectively), $k_1$, $k_2$, and t are the observed first-order rate constants and time. Further, a selected parallel multiple first order process may further comprise at least one zero order process, for example, as follows:

$$S_t = S_o + k_o t + (S_{\infty 1}-S_o)*(1-e^{-k1t}) + (S_{\infty 2}-S_o)*(1-e^{-k2t}) + (S_{\infty 3}-S_o)*(1-e^{-k3t}) \qquad \text{(Eqn. 16)}$$

where $S_o$, $S_t$ are initial and intermediate signals, $S_{\infty 1}$, $S_{\infty 2}$, $S_{\infty 3}$, are end-point signals (related to $k_1$, $k_2$, $k_3$, respectively), $k_1$, $k_2$, $k_3$, are the observed first-order rate constants, $k_o$ is a zero order rate constant, and t is time.

Further, a selected parallel multiple first order process may further comprise at least one quadratic or square root term.

In a further embodiment of a parallel multiple first order process, for example, wherein the measured signal response curve comprises a measurement of current over time, the parallel multiple first order process may comprise the following:

$$S_t = S_0 S_1 * e^{-k1*t} + S_2 * e^{-k2*t} + \text{final\_Bkgrd} \qquad \text{Eqn. 20}$$

where $S_0$ is response at t=0, t is time, $S_t$ is a total signal at time t, $S_1$ and $S_2$ are signals at time t consistent with two processes associated with apparent rate constants $k_1$ and $k_2$, and final_bkgrd is an estimated signal response at completion of a reaction used to obtain the measured signal. In one embodiment, the area under the predicted response curve is obtained by integration. In a related embodiment, before the integration is performed the final_bkgrd value is used to perform a background subtraction correction of the predicted response curve and the measurement correlated to the amount or concentration of glucose corresponds to the area under the predicted response curve.

In a further embodiment of a parallel multiple first order process, for example, wherein the measured signal response curve comprises a measurement of current over time, the parallel multiple first order process may comprise the following:

$$S_t = S_1 * e^{-k1*t} + S_2 * e^{-k2*t} + \text{final\_Bkgrd} \qquad \text{Eqn. 21}$$

where t is time, $S_t$ is a total signal at time t, $S_1$ and $S_2$ are signals at time t consistent with two processes associated with apparent rate constants $k_1$ and $k_2$, and final_bkgrd is an estimated signal response at completion of a reaction used to obtain the measured signal. As just described, the area under the predicted response curve may be obtained by integration. Further, before the integration is performed the final_bkgrd value may be used to perform a background subtraction correction of the predicted response curve, and the measurement correlated to the amount or concentration of glucose corresponds to the area under the predicted response curve.

In another aspect of the present invention, the mathematical model comprises an $n^{th}$ order process, for example, as follows:

$$S_t = S_\infty(\pm)[k(n-1)*t(\pm)(S_\infty - S_o)^{1-n}]^{1/(1-n)} \qquad \text{(Eqn. 8)}$$

where $S_o$, $S_t$, and $S_\infty$ are initial, intermediate, and end-point signals, k and t are the observed rate constant and time, n is the order of the process, where n does not equal 1, and for (±) the first function (−) is used for data that increase in magnitude as a function of time, and the second function (+) is used for the reverse case, correspondingly for (±) the first function (+) is used for data that increase in magnitude as a function of time, and the second function (−) is used for the reverse case.

In yet a further aspect of the present invention, the mathematical model comprises a flux model, for example, as follows:

$$S_t = S_o + (S_\infty - S_o)\left[1 + 2\sum_{i=0}^{\infty} (-1)^i \exp(-k_i t)\right] \qquad \text{(Eqn. 9)}$$

where $S_o$, $S_t$, and $S_\infty$ are initial, intermediate, and final (or end-point) signals, $k_i = k_i^2 \pi^2$, k is the characteristic diffusion rate constant, t is time, and i is a dummy-variable.

In one aspect of the present invention, for example, when at least three data points are obtained from the kinetic region of the measured signal response curve, these data points may be used to estimate the half-life of the measured signal. In one embodiment, the estimate of the half-life ($t_{1/2}$) further may comprise, estimating a rate constant (k): In one embodiment, such an estimate is carried out using a first order model, for example, as follows:

$$S_t = S_\infty - (S_\infty - S_o)e^{-k1} \qquad \text{(Eqn. 1)}$$

where $S_o$, $S_t$, and $S_\infty$ are initial, intermediate, and end-point signals, k and t are the observed first-order rate constant and time, respectively, wherein estimating the rate constant is performed by a method comprising plotting the natural log of signal ($S_t - S_o$) over time, where the slope of the resulting line corresponds to an estimate of k, and the half-life of the signal is calculated by using $t_{1/2} = \ln 2/k$.

In a further aspect of the present, invention, the analyte, for example, glucose, may be extracted by the sampling system into one or more collection reservoirs to obtain a concentration of the glucose in a reservoir. In one embodiment, the sampling system, comprising the collection reservoirs, is in contact with the skin or mucosal surface of the subject and the analyte is extracted using an iontophoretic current applied to the skin or mucosal surface. The collection reservoir(s) may comprise an enzyme composition, comprising an enzyme that reacts with the extracted analyte, e.g., glucose, to produce an electrochemically detectable signal. In one aspect of the invention, wherein the analyte is glucose, the enzyme may be glucose oxidase.

In another embodiment, the present invention describes a method for compensating for an incomplete reaction involving the detection of an analyte by predicting a background signal. This method also employs the predictive-kinetic methods of the present invention, as described herein.

The present invention also includes one or more microprocessors programmed to perform the calculations of the predictive-kinetic methods described herein. Such microprocessors may be further programmed to control associated devices, including, but not limited to, a sampling device, a sensing device, a power source, displays, etc.

The present invention also includes monitoring systems employing the methods described herein for frequent measurement an analyte amount or concentration present in a biological system. In one aspect, a monitoring system of the present invention comprises a sampling device for extracting the analyte from the biological system into at least one collection reservoir to obtain a concentration of the analyte in the reservoir. Typically, the collection reservoir is in contact with the skin or mucosal surface of the biological system. In one embodiment, the analyte is extracted using an iontophoretic current applied to the skin or mucosal surface. The collection reservoir may comprise an enzyme, or enzymes, used to produce an electrochemically detectable signal(s) corresponding to the analyte(s) of interest. Signals are detected using a sensing device. In a preferred embodiment the analyte comprises glucose and the enzyme comprises glucose oxidase. One or more microprocessors are programmed to control, for example, the sampling, sensing, computations employing the predictive-kinetic methods described herein, and displays of resulting values.

These and other embodiments of the present invention will readily occur to those of ordinary skill in the art in view of the disclosure herein.

BRIEF DESCRIPTION OF THE FIGURES

FIG. 13 presents the formulae for some data processing models that may be useful in the practice of the present invention.

FIG. 14 presents typical time dependent responses of the biographer glucose monitor to different concentrations of glucose (open squares, 0.06 mM glucose; open triangles, 0.045 mM glucose; X, 0.03 mM glucose; *, 0.015 mM glucose; open diamond, 0.00888 mM glucose; and, +, 0.00267 mM glucose).

FIG. 15 presents integrated responses from the data presented in FIG. 14, after background correction using the current at 405 seconds.

FIG. 16 presents fitted and experimental curves corresponding to background corrected experimental data from FIG. 15, wherein the curve fitting was carried out employing a predictive-kinetic method (Eqn. 19).

FIG. 17 presents fitted and experimental data for different levels of glucose corresponding to data from FIG. 14, wherein the curve fits were carried out employing a predictive-kinetic method (Eqn. 21). In the figure, open squares, 0.06 mM glucose; open triangles, 0.045 mM glucose; X, 0.03 mM glucose; *, 0.015 mM glucose; open diamond, 0.00888 mM glucose; +, 0.00267 mM glucose; and the lines connecting the data points correspond to the fitted curve predicted by the method.

FIG. 18 presents integrated responses from fitted current after background correction using the predicted background current that was obtained in FIG. 17, where the data fit range was 30-405 seconds.

FIG. 19 presents background current (nA) plotted as a function of concentration (mM). In the figure, open circles correspond to measured background values at 405 seconds, closed circles correspond to predicted background values, the dark solid line corresponds to a linear regression of measured background values, and the light solid line corresponds to a linear regression of predicted background values.

DETAILED DESCRIPTION OF THE INVENTION

Figure 1:
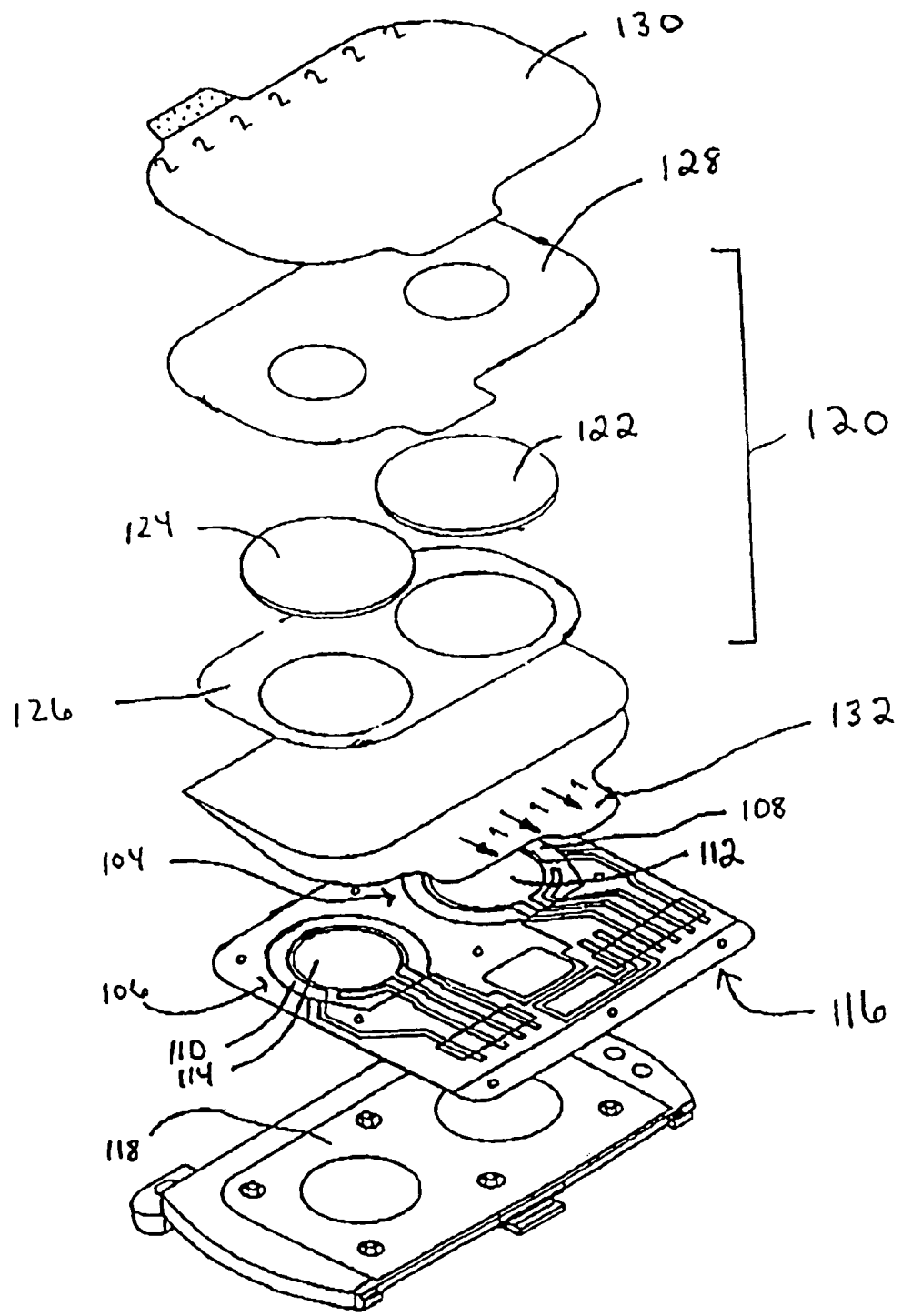
FIG. 1 is an exploded pictorial representation of components from an exemplary sampling system.

All publications, patents and patent applications cited herein are hereby incorporated by reference in their entireties.

1. Definitions

It is to be understood that the terminology used herein is for the purpose of describing particular embodiments only, and is not intended to be limiting. As used in this specification and the appended claims, the singular forms "a", "an" and "the" include plural referents unless the context clearly dictates otherwise. Thus, for example, reference to "a reservoir" includes a combination of two or more such reservoirs, reference to "an analyte" includes mixtures of analytes, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "microprocessor" refers to a computer processor contained on an integrated circuit chip, such a processor may also include memory and associated circuits. A microprocessor may further comprise programmed instructions to execute or control selected functions, computational methods, switching, etc. Microprocessors and associated devices are commercially available from a number of sources, including, but not limited to, Cypress Semiconductor Corporation, San Jose, Calif.; IBM Corporation, White Plains, N.Y.; Applied Microsystems Corporation, Redmond, Wash.; Intel Corporation, Chandler, Ariz.; and, National Semiconductor, Santa Clara, Calif.

The terms "analyte" and "target analyte" are used to denote any physiological analyte of interest that is a specific substance or component that is being detected and/or measured in a chemical, physical, enzymatic, or optical analysis—as long as the detection/measurement is obtained over time (e.g., is time-dependent and provides a response curve), the predictive-kinetic methods of the present invention can be applied. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device," "sampling mechanism" or "sampling system" refers to any device and/or associated method for obtaining a sample from a biological system for the purpose of determining the concentration of an analyte of interest. Such "biological systems" include any biological system from which the analyte of interest can be extracted, including, but not limited to, blood, interstitial fluid, perspiration and tears. Further, a "biological system" includes both living and artificially maintained systems. The term "sampling" mechanism refers to extraction of a substance from the biological system, generally across a membrane such as the stratum corneum or mucosal membranes, wherein said sampling is invasive, minimally invasive, semi-invasive or non-invasive. The membrane can be natural or artificial, and can be of plant or animal nature, such as natural or artificial skin, blood vessel tissue, intestinal tissue, and the like. Typically, the sampling mechanism is in operative contact with a "reservoir," or "collection reservoir," wherein the sampling mechanism is used for extracting the analyte from the biological system into the reservoir to obtain the analyte in the reservoir. Non-limiting examples of sampling techniques include iontophoresis, sonophoresis (see, e.g., International Publication No. WO 91/12772, published 5 Sep. 1991; U.S. Pat. No. 5,636,632), suction, electroporation, thermal poration, passive diffusion (see, e.g., International Publication Nos.: WO 97/38126 (published 16 Oct. 1997); WO 97/42888, WO 97/42886, WO 97/42885, and WO 97/42882 (all published 20 Nov. 1997); and WO 97/43962 (published 27 Nov. 1997)), microfine (miniature) lances or cannulas, subcutaneous implants or insertions, and laser devices (see, e.g., Jacques et al. (1978) J. Invest. Dermatology 88:88-93; International Publication WO 99/44507, published Sep. 10, 1999; International Publication WO 99/44638, published Sep. 10, 1999; and International Publication WO 99/40848, published Aug. 19, 1999). Iontophoretic sampling devices are described, for example, in International Publication No. WO 97/24059, published 10 Jul. 1997; European Patent Application EP 0942 278, published 15 Sep. 1999; International Publication No. WO 96/00110, published 4 Jan. 1996; International Publication No. WO 97/10499, published 2 Mar. 1997; U.S. Pat. Nos. 5,279,543; 5,362,307; 5,730,714; 5,771,890; 5,989,409; 5,735,273; 5,827,183; 5,954,685 and 6,023,629, all of which are herein incorporated by reference in their entireties. Further, a polymeric membrane may be used at, for example, the electrode surface to block or inhibit access of interfering species to the reactive surface of the electrode.

The term "physiological fluid" refers to any desired fluid to be sampled, and includes, but is not limited to, blood, cerebrospinal fluid, interstitial fluid, semen, sweat, saliva, urine and the like.

The term "artificial membrane" or "artificial surface," refers to, for example, a polymeric membrane, or an aggregation of cells of monolayer thickness or greater which are grown or cultured in vivo or in vitro, wherein said membrane or surface functions as a tissue of an organism but is not actually derived, or excised, from a pre-existing source or host.

A "monitoring system" refers to a system useful for obtaining frequent measurements of a physiological analyte present in a biological system. Such a system typically includes, but is not limited to, sampling mechanism, sensing mechanism, and a microprocessor mechanism in operative communication with the sampling mechanism and the sensing mechanism.

A "measurement cycle" typically comprises extraction of an analyte from a subject, using, for example, a sampling device, and sensing of the extracted analyte, for example, using a sensing device, to provide a measured signal, for example, a measured signal response curve. A complete measurement cycle may comprise one or more sets of extraction and sensing.

The term "frequent measurement" refers to a series of two or more measurements obtained from a particular biological system, which measurements are obtained using a single device maintained in operative contact with the biological system over a time period in which a series of measurements (e.g, second, minute or hour intervals) is obtained. The term thus includes continual and continuous measurements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

The term "transdermal" includes both transdermal and transmucosal techniques, i.e., extraction of a target analyte across skin, e.g., stratum corneum, or mucosal tissue. Aspects of the invention which are described herein in the context of "transdermal," unless otherwise specified, are meant to apply to both transdermal and transmucosal techniques.

The term "transdermal extraction," or "transdermally extracted" refers to any sampling method, which entails extracting and/or transporting an analyte from beneath a tissue surface across skin or mucosal tissue. The term thus includes extraction of an analyte using, for example, iontophoresis (reverse iontophoresis), electroosmosis, sonophoresis, microdialysis, suction, and passive diffusion. These methods can, of course, be coupled with application of skin penetration enhancers or skin permeability enhancing technique such as various substances or physical methods such as tape stripping or pricking with micro-needles. The term "transdermally extracted" also encompasses extraction techniques which employ thermal poration, laser microporation, electroporation, microfine lances, microfine cannulas, subcutaneous implants or insertions, combinations thereof, and the like.

The term "iontophoresis" refers to a method for transporting substances across tissue by way of an application of electrical energy to the tissue. In conventional iontophoresis, a reservoir is provided at the tissue surface to serve as a container of (or to provide containment for) material to be transported. Iontophoresis can be carried out using standard methods known to those of skill in the art, for example by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode). For example, see U.S. Pat. Nos. 5,771,890 and 6,023,629 and PCT Publication No. WO 96/00109, published 4 Jan. 1996.

The term "reverse iontophoresis" refers to the movement of a substance from a biological fluid across a membrane by way of an applied electric potential or current. In reverse iontophoresis, a reservoir is provided at the tissue surface to receive the extracted material, as used in the GlucoWatch®

(Cygnus, Inc., Redwood City, Calif.) biographer glucose monitor (See, e.g., Tamada et al. (1999) JAMA 282:1839-1844).

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing mechanism," or "biosensor device" encompasses any device that can be used to measure the concentration or amount of an analyte, or derivative thereof, of interest. Preferred sensing devices for detecting blood analytes generally include electrochemical devices, optical and chemical devices and combinations thereof. Examples of electrochemical devices include the Clark electrode system (see, e.g., Updike, et al., (1967) Nature 214:986-988), and other amperometric, coulometric, or potentiometric electrochemical devices, as well as, optical methods, for example UV detection.

A "biosensor" or "biosensor device" includes, but is not limited to, a "sensor element" that includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, and silver, as well as, oxides, and dioxides, thereof, and combinations or alloys of the foregoing, which may include carbon as well. Some catalytic materials, membranes, and fabrication technologies suitable for the construction of amperometric biosensors are described by Newman, J. D., et al.(1995) Analytical Chemistry 67:4594-4599.

The "sensor element" can include components in addition to the sensing electrode, for example, it can include a "reference electrode" and a "counter electrode." The term "reference electrode" is used to mean an electrode that provides a reference potential, e.g., a potential can be established between a reference electrode and a working electrode. The term "counter electrode" is used to mean an electrode in an electrochemical circuit that acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are preferred.

In one embodiment, the "counter electrode" of the "sensor element" comprises a "bimodal electrode." The term "bimodal electrode" typically refers to an electrode which is capable of functioning non-simultaneously as, for example, both the counter electrode (of the "sensor element") and the iontophoretic electrode (of the "sampling mechanism") as described, for example, U.S. Pat. No. 5,954,685.

The terms "reactive surface," and "reactive face" are used interchangeably herein to mean the surface of the sensing electrode that: (1) is in contact with the surface of an ionically conductive material which contains an analyte or through which an analyte, or a derivative thereof, flows from a source thereof; (2) is comprised of a catalytic material (e.g., a platinum group metal, platinum, palladium, rhodium, ruthenium, or nickel and/or oxides, dioxides and combinations or alloys thereof) or a material that provides sites for electrochemical reaction; (3) converts a chemical signal (for example, hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a hydrogel, a sponge or pad (e.g., soaked with an electrolytic solution), or any other material that can contain an electrolyte and allow passage of electrochemically active species, especially the analyte of interest. Some exemplary hydrogel formulations are described in WO 97/02811, published Jan. 30, 1997. The ionically conductive material may comprise a biocide. For example, during manufacture of an autosensor assembly, one or more biocides may be incorporated into the ionically conductive material. Biocides of interest include, but are not limited to, compounds such as chlorinated hydrocarbons; organometallics; hydrogen releasing compounds; metallic salts; organic sulfur compounds; phenolic compounds (including, but not limited to, a variety of Nipa Hardwicke Inc. liquid preservatives registered under the trade names Nipastat®, Nipaguard®, Phenosept®, Phenonip®, Phenoxetol®, and Nipacide®); quaternary ammonium compounds; surfactants and other membrane-disrupting agents (including, but not limited to, undecylenic acid and its salts), combinations thereof, and the like.

The term "buffer" refers to one or more components which are added to a composition in order to adjust or maintain the pH of the composition.

The term "electrolyte" refers to a component of the ionically conductive medium which allows an ionic current to flow within the medium. This component of the ionically conductive medium can be one or more salts or buffer components, but is not limited to these materials.

The term "collection reservoir" is used to describe any suitable containment method or device for containing a sample extracted from a biological system. For example, the collection reservoir can be a receptacle containing a material which is ionically conductive (e.g., water with ions therein), or alternatively it can be a material, such as a sponge-like material or hydrophilic polymer, used to keep the water in place. Such collection reservoirs can be in the form of a hydrogel (for example, in the shape of a disk or pad). Hydrogels are typically referred to as "collection inserts." Other suitable collection reservoirs include, but are not limited to, tubes, vials, strips, capillary collection devices, cannulas, and miniaturized etched, ablated or molded flow paths.

A "collection insert layer" is a layer of an assembly or laminate comprising a collection reservoir (or collection insert) located, for example, between a mask layer and a retaining layer.

A "laminate" refers to structures comprised of, at least, two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, chemical compounds such as, cyanoacrylate adhesives, and epoxies, as well as adhesives having such physical attributes as, but not limited to, the following: pressure sensitive adhesives, thermoset adhesives, contact adhesives, and heat sensitive adhesives.

A "collection assembly" refers to structures comprised of several layers, where the assembly includes at least one collection insert layer, for example a hydrogel. An example of a collection assembly as referred to in the present invention is a mask layer, collection insert layer, and a retaining layer where the layers are held in appropriate functional relationship to each other but are not necessarily a laminate (i.e., the layers may not be bonded together. The layers may, for example, be held together by interlocking geometry or friction).

The term "mask layer" refers to a component of a collection assembly that is substantially planar and typically contacts both the biological system and the collection insert layer. See, for example, U.S. Pat. Nos. 5,735,273, 5,827,183, and 6,201,979, all herein incorporated by reference.

The term "gel retaining layer" or "gel retainer" refers to a component of a collection assembly that is substantially planar and typically contacts both the collection insert layer and the electrode assembly.

The term "support tray" typically refers to a rigid, substantially planar platform and is used to support and/or align the electrode assembly and the collection assembly. The support tray provides one way of placing the electrode assembly and the collection assembly into the sampling system.

An "autosensor assembly" refers to a structure generally comprising a mask layer, collection insert layer, a gel retaining layer, an electrode assembly, and a support tray. The autosensor assembly may also include liners where the layers are held in approximate, functional relationship to each other. Exemplary collection assemblies and autosensor structures are described, for example, in International Publication WO 99/58190, published 18 Nov. 1999; and U.S. Pat. Nos. 5,735,273 and 5,827,183. The mask and retaining layers are preferably composed of materials that are substantially impermeable to the analyte (chemical signal) to be detected; however, the material can be permeable to other substances. By "substantially impermeable" is meant that the material reduces or eliminates chemical signal transport (e.g., by diffusion). The material can allow for a low level of chemical signal transport, with the proviso that chemical signal passing through the material does not cause significant edge effects at the sensing electrode.

The terms "about" or "approximately" when associated with a numeric value refers to that numeric value plus or minus 10 units of measure (i.e. percent, grams, degrees or volts), preferably plus or minus 5 units of measure, more preferably plus or minus 2 units of measure, most preferably plus or minus 1 unit of measure.

By the term "printed" is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, electroplating, laminating, or the like.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

"Parameter" refers to an arbitrary constant or variable so appearing in a mathematical expression that changing it give various cases of the phenomenon represented (McGraw-Hill Dictionary of Scientific and Technical Terms, S. P. Parker, ed., Fifth Edition, McGraw-Hill Inc., 1994). In the context of the GlucoWatch° (Cygnus, Inc., Redwood City, Calif.) biographer, a parameter is a variable that influences the value of the blood glucose level as calculated by an algorithm.

"Decay" refers to a gradual reduction in the magnitude of a quantity, for example, a current detected using a sensor electrode where the current is correlated to the concentration of a particular analyte and where the detected current gradually reduces but the concentration of the analyte does not.

2. General Overview of the Invention

Before describing the present invention in detail, it is to be understood that this invention is not limited to particular types of microprocessors, monitoring systems, computational methods or process parameters, as use of such particulars may be selected in view of the teachings of the present specification. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Figure 2:
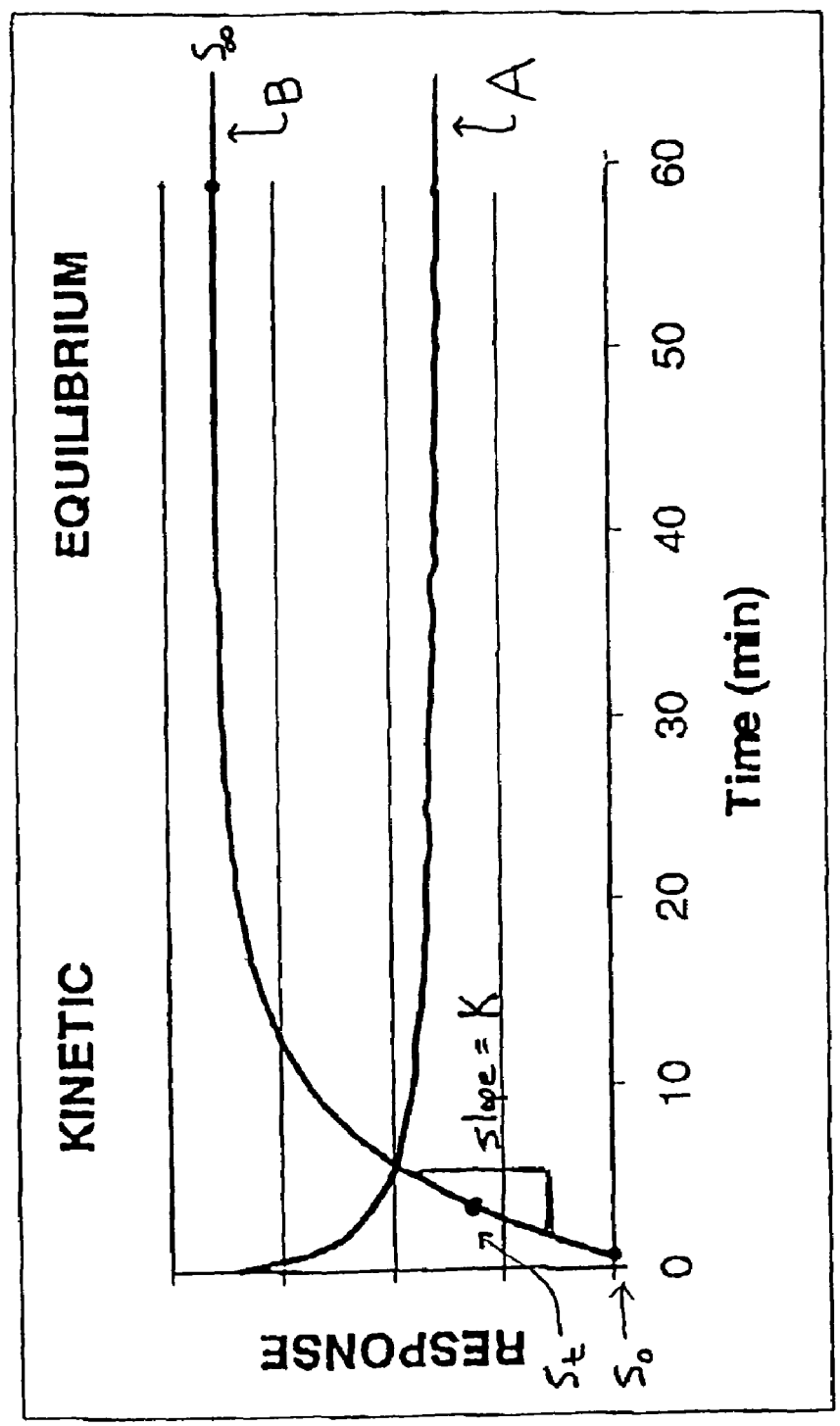
FIG. 2 illustrates kinetic and equilibrium regions of the response of a biosensor to an analyte. The figure generically represents two exemplary situations to which the predictive-kinetic methods of the present invention can be applied. In the figure, curve A corresponds, for example, to an amperometric (current) signal obtained from a sensor. The end-point value A, in this case, corresponds essentially to a final background signal after depletion of the analyte-related signal. The area under curve A corresponds to a value related to analyte amount or concentration. Curve B corresponds to an integrated form of curve A, or alternatively, a situation in which, for example, charge is directly measured by the sensor (instead of current). Accordingly, if curve A is a current signal response, then curve B is the corresponding charge signal response curve. In this case the end-point value B corresponds to an end-point analyte-related value, that is, a value related to analyte amount or concentration (i.e., the area under curve A).

There are many methods of measuring an analyte that rely on correlation of a measured signal (e.g., an amperometric signal) that is subsequently related to analyte amount or concentration. Such analytically useful signals typically have kinetic and equilibrium components. FIG. 2 shows two exemplary signals and their corresponding kinetic and equilibrium regions. In this regard, electrode sensor elements typically have kinetic and equilibrium regions of response over time. For example, when plotting sensor response (i.e., generated signal) against time, there may be a period of rapidly changing signal (e.g., increasing or decreasing signal) corresponding to a kinetic region, followed by a plateau corresponding to an equilibrium region. Rate methods for determining an analyte concentration based on a detected signal can be rapid and modified to include certain corrections, for example a background correction. However, such traditional rate methods have the following disadvantages: large variable dependencies; limited linear ranges; high dependency on noise; and, low sensitivity. Rate methods, for example, can have a high variability related to changes in the temperature at which the signal is being collected.

Equilibrium methods have certain advantages such as, small variable dependencies, extended linear ranges, and lower dependence on signal noise. However, when using such equilibrium methods the aquisition of data is slow and typically requires background correction as well. Further, in such methods there is a higher chance of side reactions taking place given the long time frame required to obtain the equilibrium data.

End-point methods for determining the amount or concentration of an analyte suffer from some of the same limitations as equilibrium methods, in particular, end-point methods require the essentially complete reaction of all analyte present in a sample. Accordingly, a signal-producing reaction correlated to analyte amount or concentration in a first sample must be completed before such a determination can be made for a second sample. Further, end-point measurements are susceptible to a higher chance of side reactions.

An alternative to equilibrium and end-point measurement methods is to take a fixed-point measurement at some time point before completion of the signal-producing reaction, thus providing a time savings relative to the end-point method (as described above). The time point used in a fixed-point measurement is typically chosen empirically, based on the type of signal being generated. Such fixed point measurements, however, are often prone to increased error due to variables affecting the signal measurement (for example, temperature, pH, electrode sensitivity). Fixed-point measurements taken during a time period when the signal is rapidly changing tend to be most error prone. However, even fixed time-point measurements taken during time periods where stable signals are typically produced can be affected by variables, for example, background noise, or spikes or pulses in the electrode response.

The present invention provides methods to reduce the time required for the measurement of analyte concentration or amount. The predictive-kinetic method of the present invention estimates the equilibrium or end-point response of a sensor (i.e., generated signal) at infinite time, i.e., effective completion of the reaction, and shows less dependence on the effects of measurement variables, such as temperature, pH, electrode sensitivity, etc. As described herein, the end-point response can be useful in several ways. In one aspect, the estimated end-point value provides an estimated final background value. In another aspect, the estimated end-point value allows more accurate estimation of analyte-related signal.

The methods of the present invention provide, for example, the following advantages: (a) reduction in the time lag between analyte extraction and measurement, and (b) reduction in the sensitivity to changes in measurement variables (e.g., reduced noise). In the method of the present invention, data from the transient, or kinetic, region of an integrated signal are used with suitable models and curve-fitting methods to predict the signal that would be measured for the system at the completion of the reaction.

Following here is a general description of one embodiment of the predictive-kinetic method of the present invention.

(i) A series of measurements of kinetic, measured data (e.g., amperometric signal) is collected using a selected sampling system. The measured data typically takes the form of a response curve (e.g., FIG. 2, curves A or B; in the figure—Curve B can represent the integrated form of curve A) with response measured relative to time. Based on the results of the measured data (e.g., comprising a series of data points over time), or preliminary transformations of the series, such as, integration to obtain an "area under the curve", a mathematical model is selected which describes the curve created by the series of measurements. That is, a mathematical model is used to fit a curve to the measured response curve. With reference to curve B of FIG. 2, such a mathematical model may be, for example, an equation (Eqn.) defining a pseudo-first-order reaction or process $$S_t = S_\infty - (S_\infty - S_o)e^{-kt} \qquad \text{(Eqn. 1)}$$

where $S_o$, $S_t$, and $S_\infty$ are initial, intermediate, and final (or end-point) signals, k and t are the observed first-order rate constant (also referred to herein as the pseudo-first order rate constant) and time, respectively. In this example the value of the parameter $S_\infty$ is what is being determined, i.e., a predicted "end-point" analyte-related value for the signal-producing reaction. Similarly, this process can be applied to curve A where the $S_\infty$ value may correspond to a final background value.

(ii) the parameters for use in the model are identified and initial values of the parameters, for example, $S_o$, $S_\infty$, and k, are estimated.

(iii) these initial values are used to predict $S_t$ at a selected number of time points (iv) an error is determined, e.g., sum of ($S_t$ measured minus $S_t$ predicted)$^2$ (v) the parameters are iteratively estimated until the error between predicted and measured values falls within an acceptable range (e.g., using a chi-square test) or until no further significant change is seen in the calculated error, at which time iterative estimation of the parameters is stopped. At this point the prediction of $S_\infty$ has been optimized.

The steps described above can be repeated any number of times to obtain a series of measurements (e.g., at least twice, and preferably frequently repeated over a time period, for example, several times an hour over a 12 or 24 hour period).

The estimated signal corresponding to $S_\infty$ is then converted to a corresponding amount or concentration of the analyte of interest, for example, where the predicted response curve is fitted to measured data of the form presented in FIG. 2, curve A, by integration of the predicted signal response curve and conversion of the end-point value obtained by integration to an analyte specific value using a calibration value.

Many models are useful in the practice of the predictive-kinetic method of the present invention, including, but not limited to the following: first order, second order, variable-order, parallel multiple first order, hyperbolic and first order, hyperbolic, linear Muller, Massart, Buck, one point fixed time, first and zero order, first and zero order with quadratic terms, first order and square root, first-order and square root with time shift, $n^{th}$ order, consecutive first order, Michaelis-Menton, flux, flux with time shift, sigmoidal, and combinations thereof (see, for example, the formulae presented in FIG. 13). Such models may comprise zero order terms as well. Some analysis methods relating to a flux model (Olsson, B., et al., Anal. Chem. 58:1046-1052, 1986) and a pseudoequilibrium model (Chen, W., et al., Analytica Chimica Acta 388:231-242, 1999) have been described for different applications. Further, using standard mathematical manipulations empirical models can be established based on collected data sets.

Further, when the predictive-kinetic methods of the present invention are used to estimate a final background value, the final background value can be used to provide a correction to the predicted response curve, for example, by background subtraction.

While not wishing to be bound by any particular theory as to why the present invention works, the following mathematical description of the predictive-kinetic method of the present invention is provided to further general understanding of the invention. The time dependent response of a reaction or process may be modeled to fit a selected system in a number of ways including a first-order model such as is presented is Equation (Eqn.) 1:

$$S_t = S_\infty - (S_\infty - S_o)e^{-kt} \qquad \text{(Eqn. 1)}$$

where $S_o$, $S_t$, and $S_\infty$ are initial, intermediate, and final signals, k and t are the observed first-order rate constant (or pseudo-first order rate constant) and time, respectively. The rate constant is considered a pseudo-first order rate constant because it accounts for the reactions and processes that are contained in the measured responses. The simultaneous estimation of $S_o$, $S_\infty$ and k is simplified by use of a linear model rather than the non-linear model in Equation 1 (Mieling, G. E., and Pardue, H. L., Anal. Chemistry 50(1978) 1611-1618). An expansion of Equation 1 as functions of $S_o$, $S_\infty$, and k using a simplified Taylor series gives an equation that is linear in parameter increments as follows:

$$S_t = S_t^o + \frac{\partial S_t^o}{\partial k}\delta k + \frac{\partial S_t^o}{\partial S_o}\delta S_o + \frac{\partial S_t^o}{\partial S_\infty}\delta S_\infty \qquad \text{(Eqn. 2)}$$

where $S_t^o$ is an initial estimate of $S_t$ expressed in terms of initial estimates of $S_o$, $S_\infty$, and k. The partial derivatives are also derived from initial estimates of $S_o$, $S_\infty$, and k inserted into the following expressions:

$$\frac{\partial S_t^o}{\partial k} = t(S_\infty - S_o) \qquad \text{(Eqn. 3a)}$$

$$\frac{\partial S_t^o}{\partial S_o} = e^{-kt} \qquad \text{(Eqn. 3b)}$$

and $$\frac{\partial S_t^o}{\partial S_\infty} = 1 - e^{-kt} \qquad \text{(Eqn. 3c)}$$

A minimization protocol, such as a multiple-linear regression program (e.g., Levenberg-Marquardt Method or simplex optimization) is used to evaluate values of $\delta k$, $\delta S_o$ and $\delta S_\infty$ which when added to initial estimate of k, $S_o$ and $S_\infty$ will give values of k, $S_o$ and $S_\infty$ which represent the best fit of the experimental data to the linearized first-order equation.

The criterion used to obtain the best fit involves the minimization of the following function:

$$\chi^2 = \frac{1}{S_{sd}^2}\Sigma\left\{S_t - S_t^o + \frac{\partial S_t^o}{\partial k}\delta k + \frac{\partial S_t^o}{\partial S_o}\delta S_0 + \frac{\partial S_t^o}{\partial S_\infty}\delta S_\infty\right\} \qquad \text{(Eqn. 4)}$$

where $\chi^2$ is chi-square, and $S_{sd}$ is the estimated standard deviation of the signal measurements. The function is minimized by setting the first derivative of $\chi^2$ with respect to $\delta S_o$, $\delta S_\infty$ and $\delta k$ equal to zero and solving the normal equations that result for the parameters $\delta S_o$, $\delta S_\infty$ and $\delta k$.

Initial estimates of $S_o$, $S_\infty$ and k, are usually in error; truncated Taylor's series in Equation 2 is only an approximation, of the nonlinear model. However, successive iterations of the procedure described above are used to obtain best estimates of these parameters. Iterations are continued until the change in $\chi^2$ is less than 0.05%. Typically, this requires 3 to 5 iterations (Mieling, G. E., and Pardue, H. L., Anal. Chemistry 50(1978) 1611-1618).

Initial estimates of $S_o$, $S_\infty$, and k, can be performed, for example, using three optional approaches: Manual, user defined values; Cornell Partial Sums; or successive integration.

Slow convergence to minimum chi-square occurs where the hypersurface does not approximate a paraboloid. The Marquardt algorithm can be used to sense this condition and a procedure approximating the method of steepest descent is used to approach the approximate parabolic hypersurface where the regression method takes over and proceeds as described above. When the process is completed, the projected change in signal may be computed. For the above-described first order model, the projected change in signal may be represented as follows:

$$\Delta S = S_\infty - S_o \qquad \text{(Eqn. 5)}$$

Following the method of the present invention, to estimate equilibrium or end-point signal for any time-dependent response not monitored to completion, multipoint data from the transient region are used with suitable models and curve-fitting methods to predict the signal that would be measured for the system at equilibrium or at completion of the reaction. This approach was illustrated above for a process that follows apparent first-order kinetics. A multiple-linear regression program is used to compute initial and equilibrium values of the signal and the first-order rate constant that represent the "best fit" of the signal vs. time data to a first-order model. Analyte concentration or amount is computed from the difference between initial and final signal values.

Although not wishing to be bound by a particular theory, the following explanation is provided to assist in understanding the method of the present invention. The method derives its reduced dependency upon measurement variables, at least in part, from the fact that the total change in signal at equilibrium is less dependent upon the variables than are the kinetic data, and the rate constant used to define the first-order process is determined independently for each sample while the analysis is in progress. Simply stated, while the reaction rate is highly variable, the extent is relatively less so. Because the method computes the signal change that would be measured if the responses were monitored to completion, the method should have characteristics more closely related to the equilibrium methods than to conventional kinetic methods provided the first-order rate constant used to fit the model is the correct one for conditions existing for each individual sample. The multiple regression method satisfies this criterion by determining the value of the rate constant, as well as the initial and final signals that represents the "best fit" to the data for each individual sample.

In the general method of the invention, a measured signal is obtained from a sensing device, which signal is related to a target analyte present in the biological system. The measured signal can be obtained using any suitable sensing methodology including, for example, methods which rely on direct contact of a sensing apparatus with a system; methods which extract samples from the system by invasive, minimally invasive, and non-invasive sampling techniques, wherein the sensing apparatus is contacted with the extracted sample; methods which rely on indirect contact of a sensing apparatus with the system; and the like. In preferred embodiments of the invention, methods are used to extract samples from a biological system using minimally invasive or non-invasive sampling techniques. The sensing apparatus used with any of the above-noted methods can employ any suitable sensing element to provide the signal including, but not limited to, physical, chemical, electrochemical, or like elements. In preferred embodiments of the invention, a biosensor is used which comprises an electrochemical sensing element.

The measured signal obtained using any of the above described methodologies is then converted into an analyte specific value of known units to provide an interpretation of the signal obtained from the sensing device. The interpretation uses a mathematical transformation to model the relationship between a measured response in the sensing device and a corresponding analyte-specific value (in the present invention, a predictive-kinetic method). Thus, a calibration step is used herein to relate, for example, an electrochemical signal (detected by a biosensor) with the concentration of a target analyte in a biological system.

The predicted analyte values can optionally be used in a subsequent step to control an aspect of the biological system. In one embodiment, predicted analyte values are used to determine when, and at what level, a constituent should be added to the biological system in order to control an aspect of the biological system. In a preferred embodiment, the analyte value can be used in a feedback control loop to control a physiological effect in the biological system.

The present invention includes, but is not limited to, methods, devices, algorithms, computer programs, equations, statistical methods, processes, and microprocessors, for use singly or in combination for measuring an analyte as described herein by the present invention. In one aspect, the present invention describes a method for measuring an analyte present in a subject. The analyte may, for example, be extracted from the subject transdermally using a sampling system that is in operative contact with a skin or mucosal surface of the subject. From this extracted sample a measured signal is obtained (e.g., using a sensing device) where the measured signal comprises a measured signal response curve derived from the extracted analyte, wherein the measured signal is specifically related to the amount or concentration of analyte, and the measured signal response curve comprises kinetic and equilibrium regions. In order to predict an analyte end-point value, a mathematical model comprising selected parameters is used, wherein the model describes the measured signal response curve. Numerous exemplary, suitable models are described herein (see, for example, FIG. 13). Further an error minimization method is typically employed. The parameters are iteratively estimated using the model and error minimization method to provide a predicted response curve corresponding to the measured signal response curve, wherein (i) the error minimization method provides a calculated error based on differences between the predicted and measured signal response curves, and (ii) the estimating is iteratively performed until the calculated error between the predicted and measured signal response curves falls within an acceptable range or until no further statistically significant change is seen in the calculated error. At that time iterative estimation of the parameters is stopped. The iterative estimation and error minimization results in a predicted response curve corresponding to the measured signal response curve, the predicted response curve yields a predicted end-point value. This predicted end-point value may correspond to a background value (e.g., FIG. 2, curve A) remaining after analyte specific signal is depleted (i.e., a final background value) or the end-point value may provide an analyte-related measurement (e.g., FIG. 2, curve B) correlated to the amount or concentration of the analyte (i.e., an end-point analyte-related value obtained, for example, by integration of the predicted response curve). An end-point analyte-related value may be further manipulated to give the amount or concentration of analyte by, for example, performing a calibration step.

In one embodiment, the present invention includes one or more microprocessors programmed to control a measurement cycle (i.e., programmed to control sampling and sensing devices) and to execute the computations of the predictive-kinetic methods described herein. Such microprocessors are useful devices alone (e.g., as a durable component of a device where the sampling and sensing devices are disposable and/or replaceable) and when placed in combination with further components (e.g., as a complete unit comprising such one or more microprocessors, a sampling device, a sensing device, and associated components such as analyte display screens, warning alert generators, power supply, etc.).

In a further embodiment, the present invention includes a monitoring system (in combination, as well as in the embodiments of its separate components) for frequent measurement of an analyte amount or concentration present in a subject. The following components of the system are in operative combination/communication:

(A) a sampling device for frequently extracting the analyte from the subject (for example, a sampling device that is adapted for extracting the analyte across a skin or mucosal surface of the subject or, in an alternative embodiment, a subcutaneous sampling device);

(B) a sensing device in operative contact with the analyte extracted by the sampling device, wherein the sensing device obtains a measured signal, comprising a measured signal response curve, from the extracted analyte, wherein the measured signal is specifically related to the amount or concentration of analyte, and the measured signal response curve comprises kinetic and equilibrium regions; and (C) one or more microprocessors capable of being in operative communication with the sampling device and the sensing device. The microprocessor is capable of controlling the sampling device and the sensing device to obtain a series of measured signals in the form of response curves at selected time intervals during a measurement period. Further, the microprocessor is capable of predicting measurement values for each measured signal in the series by employing (i) a mathematical model comprising selected parameters, wherein the model describes the measured signal response curve, and (ii) an error minimization method, to iteratively estimate values of the parameters using the model and error minimization method to provide a predicted response curve corresponding to the measured signal response curve. The error minimization method provides a calculated error based on differences between the predicted and measured signal response curves. The estimating is iteratively performed until the calculated error between the predicted and measured signal response curves falls within an acceptable range or until no further statistically significant change is seen in the calculated error, at which time iterative estimation of the parameters is stopped. This iterative estimation and error minimization results in a predicted response curve corresponding to the measured signal response curve and the predicted response curve yields a predicted end-point value. In some embodiments, each predicted end-point analyte-related value of the series may be correlated with a measurement value indicative of the amount or concentration of analyte present in the subject.

The above general methods and devices can, of course, be used with a wide variety of detection systems, target analytes, and/or sensing techniques. The determination of particularly suitable combinations is within the skill of the ordinarily skilled artisan when directed by the present disclosure. Although these methods are broadly applicable to measuring any chemical analyte and/or substance in a system, the invention is expressly exemplified for use in a transdermal sampling system which uses an electrochemical biosensor to quantify or qualify glucose or a glucose metabolite.

3. Exemplary Sampling Systems

An automatic sampling system may be used to monitor levels of analyte. One such exemplary sampling system is described herein for monitoring glucose levels in a biological system via the transdermally extraction of the analyte (e.g., glucose) from the biological system, particularly an animal subject. Transdermal extraction is carried out by applying an electrical current or ultrasonic radiation to a tissue surface at a collection site. The electrical current is used to extract small amounts of glucose from the subject into a collection reservoir. The collection reservoir is in contact with a sensor element (biosensor) which provides for measurement of glucose concentration in the subject. As glucose is transdermally extracted into the collection reservoir, the analyte reacts with the glucose oxidase within the reservoir to produce hydrogen peroxide. The presence of hydrogen peroxide generates a current at the biosensor electrode that is directly proportional to the amount of hydrogen peroxide in the reservoir. This current provides a signal which can be detected and interpreted (for example, employing the predictive-kinetic method described herein) by an associated system controller to provide a glucose concentration value or amount for display.

In the use of the sampling system, a collection reservoir is contacted with a tissue surface, for example, on the stratum corneum of a subject's skin. An electrical current is then applied to the tissue surface in order to extract glucose from the tissue into the collection reservoir. Extraction is carried out, for example, frequently over a selected period of time. The collection reservoir is analyzed, at least periodically and typically frequently, to measure glucose concentration therein. The measured value correlates with the subject's blood glucose level.

To sample the analyte, one or more collection reservoirs are placed in contact with a tissue surface on a subject. The ionically conductive material within the collection reservoir is also in contact with an electrode (for reverse iontophoretic extraction) which generates a current sufficient to extract glucose from the tissue into the collection reservoir. Referring to FIG. 1, an exploded view of exemplary components comprising one embodiment of an autosensor for use in an iontophoretic sampling system is presented. The autosensor components include two biosensor/iontophoretic electrode assemblies, 104 and 106, each of which have an annular iontophoretic electrode, respectively indicated at 108 and 110, which encircles a biosensor electrode 112 and 114. The electrode assemblies 104 and 106 are printed onto a polymeric substrate 116 which is maintained within a sensor tray 118. A collection reservoir assembly 120 is arranged over the electrode assemblies, wherein the collection reservoir assembly comprises two hydrogel inserts 122 and 124 retained by a gel retaining layer 126 and mask layer 128. Further release liners may be included in the assembly, for example, a patient liner 130, and a plow-fold liner 132. In an alternative embodiment, the electrode assemblies can include bimodal electrodes. A polyurethane mask layer 128 as described in PCT Publication No. WO 97/10356, published 20 Mar. 1997, may be present. Other embodiments of the autosensor are described in WO 99/58190, published 18 Nov. 1999.

The mask and retaining layers are preferably composed of materials that are substantially impermeable to the analyte (e.g., glucose) to be detected (see, for example, U.S. Pat. Nos. 5,735,273, and 5,827,183). By "substantially impermeable" is meant that the material reduces or eliminates analyte transport (e.g., by diffusion). The material can allow for a low level of analyte transport, with the proviso that the analyte that passes through the material does not cause significant edge effects at the sensing electrode used in conjunction with the mask and retaining layers. Examples of materials that can be used to form the layers include, but are not limited to, polyester, polyester derivatives, other polyester-like materials, polyurethane, polyurethane derivatives and other polyurethane-like materials.

The components shown in exploded view in FIG. 1 are intended for use in a automatic sampling system which is configured to be worn like an ordinary wristwatch, as described in PCT Publication No. WO 96/001 10, published 4 Jan. 1996. The wristwatch housing can further include suitable electronics (e.g., one or more microprocessor(s), memory, display and other circuit components) and power sources for operating the automatic sampling system. The one or more microprocessors may control a variety of functions, including, but not limited to, control of a sampling device, a sensing device, aspects of the measurement cycle (for example, timing of sampling and sensing, and alternating polarity between electrodes), connectivity, computational methods, different aspects of data manipulation (for example, acquisition, recording, recalling, comparing, and reporting), etc.

The sensing electrode can be, for example, a Pt-comprising electrode configured to provide a geometric surface area of about 0.1 to 3 $cm^2$, preferably about 0.5 to 2 $cm^2$, and more preferably about 1 $cm^2$. This particular configuration is scaled in proportion to the collection area of the collection reservoir used in the sampling system of the present invention, throughout which the extracted analyte and/or its reaction products will be present. The electrode composition is formulated using analytical- or electronic-grade reagents and solvents which ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants (e.g., anti-oxidants), and the solvents in particular are selected for high volatility in order to reduce washing and cure times. Some electrode embodiments are described in European Patent Publication 0 942 278 A2, published Sept. 15, 1999.

The reactive surface of the sensing electrode can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (Analytical Chemistry 67(24), 4594-4599, 1995).

Any suitable iontophoretic electrode system can be employed, an exemplary system uses a silver/silver chloride (Ag/AgCl) electrode system. The iontophoretic electrodes are formulated typically using two performance criteria: (1) the electrodes are capable of operation for extended periods, preferably periods of up to 24 hours or longer; and (2) the electrodes are formulated to have high electrochemical purity in order to operate within the present system which requires extremely low background noise levels. The electrodes must also be capable of passing a large amount of charge over the life of the electrodes. With regard to operation for extended periods of time, Ag/AgCl electrodes are capable of repeatedly forming a reversible couple which operates without unwanted electrochemical side reactions (which could give rise to changes in pH, and liberation of hydrogen and oxygen due to water hydrolysis). The Ag/AgCl electrode is thus formulated to withstand repeated cycles of current passage in the range of about 0.01 to 1.0 mA per cm² of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also typically formulated using analytical- or electronic-grade reagents and solvents, and the polymer binder composition is selected to be free of electrochemically active contaminants which could diffuse to the biosensor to produce a background current.

The automatic sampling system can transdermally extract the sample over the course of a selected period of time using reverse iontophoresis. The collection reservoir comprises an ionically conductive medium, preferably the hydrogel medium described hereinabove. A first iontophoresis electrode is contacted with the collection reservoir (which is typically in contact with a target, subject tissue surface), and a second iontophoresis electrode is contacted with either a second collection reservoir in contact with the tissue surface, or some other ionically conductive medium in contact with the tissue. A power source provides an electrical potential between the two electrodes to perform reverse iontophoresis in a manner known in the art. As discussed above, the biosensor selected to detect the presence, and possibly the level, of the target analyte (for example, glucose) within a reservoir is also in contact with the reservoir.

In practice, an electric potential (either direct current or a more complex waveform) is applied between the two iontophoresis electrodes such that current flows from the first electrode through the first conductive medium into the skin, and back out from the skin through the second conductive medium to the second electrode. This current flow extracts substances through the skin into the one or more collection reservoirs through the process of reverse iontophoresis or electroosmosis. The electric potential may be applied as described in PCT Publication No. WO 96/00110, published 4 Jan. 1996.

As an example, to extract glucose, the applied electrical current density on the skin or tissue can be in the range of about 0.01 to about 2 mA/cm². In order to facilitate the extraction of glucose, electrical energy can be applied to the electrodes, and the polarity of the electrodes can be, for example, alternated so that each electrode is alternately a cathode or an anode. The polarity switching can be manual or automatic. A device and method for sampling of substances using alternating polarity is described in U.S. Pat. No. 5,771,890, issued Jun. 30, 1998.

When a bimodal electrode is used (e.g., U.S. Pat. No. 5,954,685, issued Sep. 21, 1999), during the reverse-iontophoretic phase, a power source provides a current flow to the first bimodal electrode to facilitate the extraction of the chemical signal into the reservoir. During the sensing phase, a separate power source is used to provide voltage to the first sensing electrode to drive the conversion of chemical signal retained in reservoir to electrical signal at the catalytic face of the sensing electrode. The separate power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode subassembly can be operated by electrically connecting the bimodal electrodes such that each electrode is capable of functioning as both an iontophoretic electrode and counter electrode along with appropriate sensing electrode(s) and reference electrode(s).

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present invention, the electrical current measured at the sensing electrode subassembly is the current that is correlated with an amount of chemical signal corresponding to the analyte.

The detected current can be correlated with the subject's blood glucose concentration (using, for example, the predictive-kinetic method described herein) so that the system controller may display the subject's actual blood glucose concentration as measured by the sampling system. Such statistical techniques can be formulated as algorithm(s) and incorporated in one or more microprocessor(s) associated with the sampling system.

In a further aspect of the present invention, the sampling/sensing mechanism and user interface may be found on separate components. Thus, the monitoring system can comprise at least two components, in which a first component comprises sampling mechanism and sensing mechanism that are used to extract and detect an analyte, for example, glucose, and a second component that receives the analyte data from the first component, conducts data processing on the analyte data to determine an analyte concentration and then displays the analyte concentration data. Typically, microprocessor functions (e.g., control of a sampling device, a sensing device, aspects of the measurement cycle, computational methods, different aspects of data manipulation or recording, etc.) are found in both components. Alternatively, microprocessing components may be located in one or the other of the at least two components. The second component of the monitoring system can assume many forms, including, but not limited to, the following: a watch, a credit card-shaped device (e.g., a "smart card" or "universal card" having a built-in microprocessor as described for example in U.S. Pat. No. 5,892,661), a pager-like device, cell phone-like device, or other such device that communicates information to the user visually, audibly, or kinesthetically.

Further, additional components may be added to the system, for example, a third component comprising a display of analyte values or an alarm related to analyte concentration, may be employed. In certain embodiments, a delivery unit is included in the system. An exemplary delivery unit is an insulin delivery unit. Insulin delivery units, both implantable and external, are known in the art and described, for example, in U.S. Pat. Nos. 5,995,860; 5,112,614 and 5,062,841. Preferably, when included as a component of the present invention, the delivery unit is in communication (e.g., wire-like or wireless communication) with the extracting and/or sensing mechanism such that the sensing mechanism can control the insulin pump and regulate delivery of a suitable amount of insulin to the subject.

Advantages of separating the first component (e.g., including the biosensor and iontophoresis functions) from the second component (e.g., including some microprocessor and display functions) include greater flexibility, discretion, privacy and convenience to the user. Having a small and lightweight measurement unit allows placement of the two components of the system on a wider range of body sites, for example, the first component may be placed on the abdomen or upper arm. This wider range of placement options may improve the accuracy through optimal extraction site selection (e.g., torso rather than extremities) and greater temperature stability (e.g., via the insulating effects of clothing). Thus, the collection and sensing assembly will be able to be placed on a greater range of body sites. Similarly, a smaller and less obtrusive microprocessor and display unit (the second component) provides a convenient and discrete system by which to monitor analytes. The biosensor readouts and control signals will be relayed via wire-like or wireless technology between the collection and sensing assembly and the display unit which could take the form of a small watch, a pager, or a credit card-sized device. This system also provides the ability to relay an alert message or signal during nighttime use, for example, to a site remote from the subject being monitored.

In one embodiment, the two components of the device can be in operative communication via a wire or cable-like connection. Operative communications between the components can be wireless link, i.e. provided by a "virtual cable," for example, a telemetry link. This wireless link can be uni- or bi-directional between the two components. In the case of more than two components, links can be a combination of wire-like and wireless.

4. Exemplary Analytes

The analyte can be any specific substance, component, or combinations thereof that one is desirous of detecting and/or measuring in a chemical, physical, enzymatic, or optical analysis. The predictive-kinetic method of the present invention may be employed as long as the detection/measurement of the analyte is time dependent, e.g., the detection measurement method provides a response curve having a kinetic region.

Analytes that can be measured using the methods of the present invention include, but are not limited to, amino acids, enzyme substrates or products indicating a disease state or condition, other markers of disease states or conditions, drugs of abuse (e.g., ethanol, cocaine), therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate and/or lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. Analytes in non-biological systems may also be evaluated using the methods of the present invention.

In preferred embodiments, the analyte is a physiological analyte of interest, for example glucose, or a chemical that has a physiological action, for example a drug or pharmacological agent.

In order to facilitate detection of the analyte, an enzyme (or enzymes) can be disposed within the one or more collection reservoirs. The selected enzyme is capable of catalyzing a reaction with the extracted analyte to the extent that a product of this reaction can be sensed, e.g., can be detected electrochemically from the generation of a current which current is detectable and proportional to the amount of the analyte which is reacted. In one embodiment of the present invention, a suitable enzyme is glucose oxidase, which oxidizes glucose to gluconic acid and hydrogen peroxide. The subsequent detection of hydrogen peroxide on an appropriate biosensor electrode generates two electrons per hydrogen peroxide molecule creating a current that can be detected and related to the amount of glucose entering the device. Glucose oxidase (GOx) is readily available commercially and has well known catalytic characteristics. However, other enzymes can also be used singly (for detection of individual analytes) or together (for detection of multiple analytes), as long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, cholesterol with a cholesterol oxidase system, and theophylline with a xanthine oxidase system.

In addition, the oxidase enzyme (used for hydrogen peroxidase-based detection) can be replaced or complemented with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea.

Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytoin), chemotherapy (e.g., adriamycin), hyperactivity (e.g., ritalin), and anti-organ-rejection (e.g., cyclosporin).

Preferably, a sensor electrode is able to detect the analyte that has been extracted into the one or more collection reservoirs when present at nominal concentration levels. Suitable exemplary biosensor electrodes and associated sampling systems as described in are described in PCT Publication Nos. WO 97/10499, published 20 Mar. 1997 and WO 98/42252, published 1 Oct. 1998.

Further, the predictive-kinetic methods of the present invention facilitate analysis of multiple analytes obtained in a single sample (e.g., a sample collected into a single reservoir using transdermal extraction), even when such multiple analytes are being detected by a common reaction product. For example, a sensing device may be used that employs several oxidase enzymes, e.g., lactate oxidase, uricase, and glucose oxidase. Each of these enzymes has the ability to generate hydrogen peroxide when contacted by their respective substrates. A single sensor sensitive to, for example, hydrogen peroxide (e.g., a platinum electrode), cannot differentiate between peroxide originating from glucose, uric acid or lactic acid. However, by employing the predictive-kinetic methods of the present invention, the apparent rate constant for each reaction and the concentration of each analyte can be resolved, that is, the predictive-kinetic method can resolve the individual contributions to overall, final, peroxide-mediated signal. Thus, with suitable computing power, the concentrations of each analyte can be obtained. Variables, such as, pH and enzyme concentration, allow manipulation of the apparent rate constants of each enzyme to aid resolution and minimize interference between components. Further, a system of weighting factors could be employed as well, where, for example, contributions by different components are weighted differently based on their known contribution to overall signal.

Typically, the reactions with substrate to form detectable product, as facilitated by different enzymes, do not interfere with one another. The predictive-kinetic methods described herein are particularly useful for detection of multiple analytes using a common reaction product, for example, hydrogen peroxide, when there are at least three-fold differences, preferably five- to ten-fold difference or higher, in the reaction rate constants for conversion of the different analytes to the common reaction product. For example, detection of glucose and urea in a single sample may be facilitated by the use of the enzymes glucose oxidase and uricase (urate oxidase) both of which yield hydrogen peroxide as the common, detectable reaction product. The $k_m$ of glucose oxidase is approximately $3.3 \times 10^{-2}$ molar and the $k_m$ of uricase is approximately $10^{-5}$ molar. For example, signals corresponding to glucose and urea can be resolved within a single signal response curve based on the apparent rate constants (i.e., the $k_m$) of the two reactions using the parallel first order predictive-kinetic model described herein.

In the example described above a common reaction product is formed (i.e., hydrogen peroxide); however, this is not a requirement. A single sensor may detect multiple analytes and/or reaction products of analytes. For example, a platinum sensor could be used to detect tyrosine and glucose in a single sample. The tyrosine is detected, for example, by direct electrochemical oxidation at a suitable electrode potential (e.g., approximately 0.6V vs. Ag/AgCl). The glucose is detected, e.g., using glucose oxidase and detecting the hydrogen peroxide reaction product. For example, signals corresponding to tyrosine and glucose can be resolved within a single signal response curve based on the apparent rate constants (i.e., the $k_m$) of the two reactions using the parallel first order predictive-kinetic model described herein.

Generally when detecting multiple analytes with a single sensor it is preferred that, within a single response curve, the primary signals corresponding to each analyte are separated in time, e.g., one analyte's reaction with the sensor is rapid ($k_1$) and a second analyte's reaction with the sensor is slower ($k_2$), i.e., $k_1 \gg k_2$.

Different sensing devices and/or sensing systems can be employed as well to distinguish between signals. For example, a first gel containing glucose oxidase associated with a first platinum sensor can be used for the detection of glucose, while a second gel containing uricase associated with a second platinum sensor can be used for the detection of urea. The predictive-kinetic methods of the present invention may then used to individually model the signal response curves generated at each sensor.

5. Employing the Predictive-Kinetic Method in Glucose Measurement

A. Predictive-Kinetic Models

The GlucoWatch biographer is a device that provides frequent and automatic glucose measurements. Glucose is extracted through the skin via electro-osmosis and measured with an amperometric biosensor. Glucose is extracted into a hydrogel of, for example, 0.18 mm in thickness, containing the enzyme, glucose oxidase. The enzyme converts the extracted glucose to hydrogen peroxide. The hydrogen peroxide is detected by a Pt/C electrode composite directly under the hydrogel. A potentiostat used to apply the polarizing voltage and collect the resulting current is part of the wearable device that displays values of the measured glucose to the user.

One variable affecting the measurement objective of the biographer is the rate of mutarotation of the α to β forms of glucose (Kurnik R. T., et al., Journal of the Electrochemical Society 145 (1998) 4119-4125). One goal of the present design of the biographer is that, in the presence of excess enzyme loading and for a given extracted glucose concentration, the same response is measured by the biographer regardless of changes in the measurement variables. However, because the mutarotation constant is dependent on changes in other measurement variables, especially temperature, a long measurement time is required to ensure complete consumption of the glucose in the hydrogel (Pardue, H. L., Kinetic Aspects of Analytical Chemistry, Anal. Chim. Acta 69 (1989) 216; Mieling, G. E., and Pardue, H. L., Anal. Chemistry 50(1978) 1611-1618.). Accordingly, some of the measurement variables that can affect the measurement objective of the biographer include mutarotation, diffusion (e.g., slow diffusion of glucose through the hydrogel), and electrode kinetics. The latter results in apparent drift in sensor sensitivity. Use of the predictive-kinetic method of the present invention in combination with the biographer measurements provides a technique that estimates the equilibrium or end-point responses of the biographer. Further, the predictive-kinetic method of present invention reduces the effects of measurement variables, such as temperature.

As described above, glucose (in a hydrogel) is converted to hydrogen peroxide, a current (in the order of nanoamps) is generated and detected over time (typically resulting in a curve that looks like curve A in FIG. 2). The current is typically integrated to provide a curve of nanocoloumb values (nC) relative to time. The resulting data can be schematically represented by curve B of FIG. 2.

To employ the predictive-kinetic method of the present invention, data from the kinetic region of the curve can be fitted to a model. For benchtop studies, described below, a first-order reaction or process fits the data well:

$$S_t = S_\infty - (S_\infty - S_o)e^{-kt} \qquad \text{(Eqn. 1)}$$

where $S_o$, $S_t$, and $S_\infty$ are initial, intermediate, and final signals, k and t are the observed first-order rate constant and time, respectively.

In one embodiment of the present invention, the method is used to predict an $S_\infty$ that corresponds to a final background value (e.g., FIG. 2, curve A). This final background value can be used to provide a background correction, for example, by using the final background value for background subtraction. In a further aspect, the method is used to predict an $S_\infty$ which corresponds to an analyte-related value, for example, after integration of the predicted signal response curve based on current, the end-point value corresponds to an equilibrium charge value (e.g., nC) which may then be further manipulated or directly converted to an amount or concentration of glucose. Accordingly, to obtain the predicted value of $S_\infty$, estimation of three values is required, $S_o$, $S_\infty$, and k. Estimates of the values are made by iteratively using initial estimated values until, via an error minimization method, the predicted curve matches the curve of the real (measured) data to within a predecided margin of error. The iterative process is repeated until error minimization is achieved.

Experimental results from benchtop studies using the biographer are described in the Experimental section below. In these studies, the biosensor was assembled and preconditioned for one hour. Ten microliters of glucose solution of known concentration was then deposited on the hydrogel. The electrode response to the glucose was monitored. The current responses were then transferred to a computer for data processing. The results presented in Example 1 (FIGS. 3 and 4) demonstrate the ability of the predictive-kinetic method of the present invention to accurately estimate end-point responses using a glucose-specific device, e.g., the biographer. End-point analyte-related values may then be correlated to glucose concentration or amount.

The results presented in Example 2 show that data using three half-lives provide a reliable estimate of the end-point charge. Further, a variance ratio was used to verify that the first-order model used was a valid option. Similar data treatment demonstrated that using a diffusion-limited, flux model (e.g., Olsson, B., et al., Anal. Chem. 58:1046-1052, 1986) also provided a valid predictive-kinetic model for the data. For the benchtop studies performed with the biographer the first-order appears to provide the best estimates of the equilibrium values. However, other models may be applied to evaluation of the data as described herein, such models include, but are not limited to diffusion limited models, a parallel multiple first order and an n-th order model that does not require knowledge of the reaction order. The parallel multiple first order can be expressed as follows:

$$S_t = S_o + (S_{\infty 1} - S_o)*(1-e^{-k_1 t}) + (S_{\infty 2} - S_o)*(1-e^{-k_2 t}) + (S_{\infty 3} - S_o)*(1-e^{-k_3 t}) + \ldots \quad \text{(Eqn. 6A)}$$

where $S_o$, $S_t$ are initial and intermediate signals, $S_{\infty 1}$, $S_{\infty 2}$, $S_{\infty 3}$, etc., are final (or end-point) signals (related to $k_1$, $k_2$, $k_3$, etc., respectively), $k_1$, $k_2$, $k_3$, etc., are the observed first-order rate constants, and t is time. This model is discussed further hereinbelow. This model is typically used in a situation where more than one first order reaction or process is occurring in parallel. In the model presented above in Eqn. 1, the optimized value of $S_\infty$ provides the predicted end-point value. As described herein, the predicted end-point value may be employed in several ways. In one aspect, the end-point analyte related value provides a measurement correlated to the amount or concentration of the analyte. Depending on the application this value may be modified, for example, by addition or subtraction of the initial signal and/or by applying calibration methods (which, for example, converts the value from current or charge to analyte amount or concentration). Using the model presented in Eqn. 6A, the end-point signal is typically represented by the following equation:

$$S_\infty = (S_{\infty 1} + S_{\infty 2} S_{\infty 3} + \ldots) + S_o \quad \text{(Eqn. 6B)}$$

Whereas the final signal change in this case is typically represented by the following relationship:

$$\Delta S_\infty = (S_{\infty 1} + S_{\infty 2} + S_{\infty 3} + \quad \text{(Eqn. 6C)}$$

Based on the teachings of the present specification and knowledge of one of ordinary skill in the art, a practitioner can choose which embodiment of the end-point value (e.g., $S_\infty$ or $\Delta S_\infty$) better represents the end-point value of interest. This choice may be guided, for example, by comparison of an end-point value to a calibration value, determined by independent methods, at a selected time point. Another approach is to plot end point values ($S_\infty$ or $\Delta S_\infty$) vs. known analyte concentration and utilize a determination of imprecision to select the best end point value. In some situations, for example where there is a high initial signal ($S_o$) which is largely attributed to background, the $\Delta S_\infty$ value may provide a better end-point value to use in determination of the corresponding amount or concentration of analyte.

In some cases, for example, where background predominates the $S_o$ value and when a background correction has been performed on the data before application of the predictive-kinetic method of the present invention, the parallel multiple first order (Eqn. 6A) may be expressed as follows:

$$S_t = S'_o + (S_{\infty 1})*(1-e^{-k_1 t}) + (S_{\infty 2})*(1-e^{-k_2 t}) + (S_{\infty 3})*(1-e^{-k_3 t}) + \quad \text{(Eqn. 7A)}$$

where $S'_o$, is an estimate of initial signal at t=0 (i.e., $S'_o$ corresponds to $S_o$ after correction for the contribution of background signal), $S_t$ is an intermediate signal, $S_{\infty 1}$, $S_{\infty 2}$, $S_{\infty 3}$, etc., are final (or end-point) signals (related to $k_1$, $k_2$, $k_3$, etc., respectively), $k_1$, $k_2$, $k_3$, etc., are the observed first-order rate constants, and t is time. In this example, an estimate of $S_\infty$ and the corresponding $\Delta S_\infty$ may be represented as follows:

$$S_\infty = (S_{\infty 1} + S_{\infty 2} + S_{\infty 3} + \ldots) \quad \text{(Eqn. 7B)}$$

$$\Delta S_\infty = (S_{\infty 1} + S_{\infty 2} + S_{\infty 3} + \ldots) - S'_o \quad \text{(Eqn. 7C)}$$

Typically in the methods of the present invention, the predicted end-point value is represented by $S_\infty$ whereas the change in the predicted end-point value relative to the initial signal is represented as $\Delta S_\infty$.

An $n^{th}$ order model can be expressed as follows:

$$S_t = S_\infty (\pm) [k(n-1)*t(\pm)(S_\infty - S_o)^{1-n}]^{1/(1-n)} \quad \text{(Eqn. 8)}$$

where $S_o$, $S_t$, and $S_\infty$ are initial, intermediate, and final (or end-point) signals, k and t are the observed rate constant and time, n is the order of the process, where n does not equal 1, and for ($\pm$) the first function (−) is used for data that increase in magnitude as a function of time, and the second function (+) is used for the reverse case, correspondingly for ($\pm$) the first function (+) is used for data that increase in magnitude as a function of time, and the second function (−) is used for the reverse case.

An exemplary flux model can be expressed as follows:

$$S_t = S_o + (S_\infty - S_o)\left[1 + 2\sum_{i=0}^{\infty}(-1)^i \exp(-k_i t)\right] \quad \text{(Eqn. 9)}$$

where $S_o$, $S_t$, and $S_\infty$ are initial, intermediate, and final (or end-point) signals, $k_i = k i^2 \pi^2$, k is the characteristic diffusion rate constant, t is time, and i is a dummy-variable. In this model, the $k_i$ values should vary by $\pi^2$ (i.e., approximately 10). This variation can be used as a control.

B. Reduced Dependency of the Predictive-Kinetic Model on Measurement Variables

Temperature was selected as a variable to demonstrate the reduced dependency of the predictive-kinetic method on measurement variables. This variable was selected because it affects the rate of mutarotation as well as the rate of physical processes such as diffusion of glucose through a hydrogel (Kurnik R. T., et al., Journal of the Electrochemical Society 145 (1998) 4119-4125). The results of these experiments are shown in Example 4. Clearly, the predictive-kinetic method gave consistent results regardless of the measurement temperature. The percent change in results observed with the predictive-kinetic method relative to temperature change was negligible. Further, regardless of the rate constant, similar end-point values were computed using the predictive-kinetic method.

Following here is a proposed explanation for the reduced dependency of the predictive-kinetic method on measurement variables. The following should not be construed to be the only mechanistic explanation possible and is provided only to possibly clarify understanding of some aspects of the invention. Because rates of reactions or processes, but not extent, can be affected by such variables as temperature, responses of analytical systems that are based on kinetic measurements (e.g., electrochemical current generated by a biosensor) exhibit dependencies on these variables. The predictive-kinetic model as used to measure an equilibrium or end-point condition has much lower dependencies on these variables because the rate of reaction controls the speed at which the system reaches the equilibrium point or end-point, but not the point itself.

The predictive-kinetic model uses kinetic data to predict the equilibrium or end-point of a reaction. This model finds the best-fit value of several parameters, including the rate constant(s) of the process (es) involved in producing the signal. Because the rate constant is one of the fit parameters it provides a correction for variables that affect the kinetic measurements, such as, temperature, diffusion constants, enzyme kinetics, etc. For example, in the case of glucose measurement using an analyte monitoring device as described here, the data set for each biosensor measurement cycle is fit individually. Accordingly, if the temperature changes occur during or between cycles then the model will fit a slightly different rate constant (e.g., Example 4).

Sweat can contain certain analytes, such as glucose, and thus potentially add a spurious signal to the analyte measurement and, accordingly, could give rise to inaccurate values. This problem may be-avoided by, for example, incorporating a probe in the device to measure and indicate the presence of sweat on the skin (e.g., the GlucoWatch biographer). However, because the predictive-kinetic method uses data in the leading edge of the response cycle (e.g., the first three half-lives), sweat episodes that occur only after this period would not affect the measurement and would allow display of that result to the user. Evaluation of the half-life profile of data from several diabetic and non-diabetic subjects showed that three minutes of the transient response is sufficient to predict the end-point signals. Therefore, sweat episodes that occur after three minutes into the response cycle will not affect the measurement.

Drift of values determined by an electrochemical current/biosensor system can also be significantly compensated by the equilibrium or end-point based measurement approach employed in the predictive-kinetic method. This approach has reduced variable dependencies on such variables as temperature, hydrogel membrane thickness, electrode kinetics, and enzyme activity such that changes in these variables during or between measurement cycles do not affect the reliability and accuracy of the glucose measurements provided to the end user.

A further example of the reduced dependency of the predictive-kinetic method on measurement variables is illustrated by the ability of the predictive-kinetic method to provide compensation for declining sensor signal. Factors responsible for decline of sensor sensitivity include, but are not limited to, the following: adsorption of proteins on the electrode surface; and reduction in enzyme activity. Often, analyte monitoring devices that rely on platinum/carbon (Pt/C) electrodes and are worn by a subject for an extended period of time show a decline in sensor response over time. One possible explanation is attenuation in the signal caused by an apparent decline in sensitivity of the underlying Pt/C electrode.

Several approaches might be used to compensate for the decline in signal is including, but not limited to, the following: (i) increasing the measurement time for a given response cycle; and (ii) changing the hydrogel/sensor component after a predetermined time period of use. However, these approaches are typically neither cost effective nor convenient to the user.

The use of the predictive-kinetic method can compensate for the effect of such sensor-based or enzyme-based signal decline in an analyte monitor because the method estimates the end-point signal consistent with complete consumption of an extracted analyte, for example, glucose in a hydrogel. Accordingly, any decline in the sensitivity of the sensor (i.e., electrode) would not influence the predicted signal. An illustration of the ability of the predictive-kinetic method to compensate for such sensor-based signal decline is presented in Example 5 with corresponding data in FIGS. 11 and 12. The results demonstrate that the predictive-kinetic approach can measure essentially all glucose extracted, regardless of the sensor sensitivity, thereby compensating for the signal decline seen with a fixed integral measurement method.

These results demonstrate the usefulness of the predictive-kinetic method applied to data obtained from a device that provides frequent and automatic analyte-related measurements. The results demonstrate that transient response from a such a device can be modeled successfully and provide (i) a reliable estimate of a steady-state signal, (ii) calibration curves similar to a steady-state model, (iii) lower dependence on measurement variables.

When the biographer is being used by a subject there is an extraction period followed by a measurement period. During the extraction period most of the analyte (i.e., extracted glucose or its conversion product, hydrogen peroxide) localizes near the reactive face of the electrode. However, some of the analyte may be dispersed throughout the hydrogel. When voltage is applied to the reactive face of the electrode in order to quantitate the signal from the analyte, this results in an initial current with a signal that decays following a pseudo-first order rate constant ($k_1$); however, in this situation a parallel multiple first order reaction is taking place as the remainder of the analyte reaches the reactive face and generates current (rate constant $k_2$). Accordingly, the parallel multiple first order model discussed herein above provides one model for the biographer when it is being used in operative contact with a subject. In this embodiment, the parallel multiple first order can be expressed as follows:

$$S_t = S_o + (S_{\infty 1} - S_o) * (1 - e^{-k_1 t}) + (S_{\infty 2} - S_o) * (1 - e^{-k_2 t}) \quad \text{(Eqn. 10)}$$

where $S_o$, $S_t$, $S_{\infty 1}$, and $S_{\infty 2}$ are initial, intermediate, and final signals (related to $k_1$ and $k_2$, respectively), $k_1$, $k_2$, and t are the observed first-order rate constants and time, respectively. In this case, the-two rate processes that determine responses from the biographer have significantly different magnitudes, $k_1 \gg k_2$. Typically, the ratio of $k_1$ to $k_2$ remains constant. Maintenance of this constant relationship may be used as a criterion of good fit of the data.

Accordingly, when predicting the end-point value (e.g., $S_\infty = S_o + S_{\infty 1} + S_{\infty 2}$) there are now a total of five parameters to be estimated for each predicted $S_t$, those parameters being $S_{\infty 1}$, $S_o$, $k_1$, $S_{\infty 2}$, and $k_2$. As discussed above these parameters are estimated and predicted values of $S_t$ iteratively generated until the error between the predicted values and the actual data points is minimized. That is, the iterative process is repeated until error minimization is achieved. The result is a final value for $S_\infty$ which is then converted to glucose amount or concentration by, for example, multiplying the value with a calibration value.

In one embodiment, a calibration value can be determined essentially as follows. $S_\infty$ is based on a measurement cycle of the biographer at a calibration point, wherein in the corresponding time frame the subject also performs, for example, a finger stick to determine the blood glucose value at the calibration point. The amount of glucose at the calibration point can be determined using, for example, a HemoCue® (Aktiebolaget Leo, Helsingborg, Sweden) clinical analyzer. The blood glucose measurement obtained is used as a single point calibration, which is used to calculate the extracted blood glucose amounts or concentrations for all subsequent GlucoWatch biographer measurements. Accordingly, the calibration value is equal to the measured blood glucose amount at the calibration time divided by the predicted nC value determined at the calibration time (i.e., $S_\infty$). Subsequent predicted nC values (i.e., $S_\infty$) are then multiplied by this calibration value to obtain blood glucose amount or concentration.

C. Optimization of Signal Measurement Time

In addition to the predictive-kinetic method described herein, the present invention also includes methods to determine if enough data points have been gathered by the biographer in order to produce reliable predicted values. Experiments performed in support of the present invention suggest that data in the kinetic portion of the curve corresponding to three or more half lives of the signal provide reliable predicted values. Accordingly, the time period through which the biographer is measuring signal can be dynamically evaluated while signal is being measured and collected. For example, typically at least three data points are collected. These data points are used to estimate a first order rate constant k by plotting the natural log of signal $(S_t-S_o)$ over time, where the slope of the resulting line corresponds to an estimate of k. To simplify, this relationship can be expressed by the following equation: $t_{1/2} = \ln 2/k$ (i.e., $t_{1/2} = 0.6293/k$).

Based on empirical observations an average optimal measurement time can typically be determined (e.g., three minutes for the biographer). However, in an alternate embodiment to ensure that at least three half lives of the signal are encompassed by this time period, an algorithm can be established that calculates $t_{1/2}$ for the signal data. This value is then multiplied by three. If the resulting value is less than the average optimal measurement time, then that measurement time is sufficient. If, however, the resulting value is greater than the average optimal measurement time, then the biographer can be instructed by the algorithm to continue its measurement cycle until three half lives of the signal (or a finite cut-off point) is achieved.

Accordingly, in a preferred embodiment of the present invention the steps of a method for determining blood glucose concentration or amount are as follows:

(i) collect current data (e.g., at least three signal values in the kinetic range);

(ii) estimate the rate constant (k) for a first order model by plotting the natural log of signal $(S_t-S_o)$ over time, where the slope of the resulting line corresponds to an estimate of k;

(iii) estimate the half-life of the signal using $t_{1/2}=\ln 2/k$;

(iv) (a) if three times the resulting value is less than the average optimal measurement time, then that measurement time is sufficient. (b) If three times the resulting half-life value is greater than the average optimal measurement time, then the biographer is instructed by an algorithm to continue its measurement cycle until three half lives of the signal (or a finite cut-off point) is achieved;

(v) the current data is integrated (resulting in nC data)— appropriate background subtraction may be performed before this step if desired;

(vi) the actual nC data is used to estimate parameters in the selected model, for example, the parallel multiple first order model, and an error is determined (e.g., sum of squares for predicted values minus actual values). This process is repeated (i.e., an iterative process) until either the error is less than a predetermined threshold error (determined, for example, using change in chi-square less than 0.05%) or there is no further change in the error upon further iteration. This error minimization steps can be carried out by a number of methods known in the art, for example, the Levenberg-Marquardt Method or simplex optimization method. (See, for example, error minimization methods described in Numerical Recipes in C, Second Edition, Cambridge Univ. Press, 1992.)

(vii) the final predicted $S_\infty$ is then converted to a blood glucose value by multiplying the predicted $S_\infty$ by a calibration value.

This method can be adapted by one of ordinary skill in the art, following the guidance of the specification in combination with what is known in the art, to employ different models that are selected to best represent the signal for a selected analyte/measurement system (for example, by changing the model in step (vi)).

D. Variations on the Parallel Multiple First Order Model

The parallel multiple first order model (PMFOM) assumes more than one first order process occurs simultaneously. The PMFOM finds the best-fit of the data by deconvoluting the measured data into separate processes, i.e., there is a segregation of processes. The best-fit parameters are then used to predict the end-point nC value of the integrated signal. However, certain components of the signal may not arise from glucose, but may be due to other electrochemical processes, e.g., Pt oxidation, background currents from impurities, interfering species, etc. In the context of determining glucose analyte amounts or concentration, only the signal (i.e., charge) arising from the glucose is of interest; other components contributing to charge are, essentially, noise.

With a sufficiently high density of current points during the measurement cycle, with which to fit the data, it is possible to include in the PMFOM as many parallel processes as are identified. In this way, the total signal is separated into its individual components, i.e., each component arising from a different process. Then only those components shown to arise from glucose can be used in the PMFOM.

For example, suppose that a PMFOM with three parallel processes is used. The total signal at time t is then the sum of the three individual processes:

$$S_t = S_o + (S_{\infty 1} - S_o)*(1-e^{-k_1 t}) + (S_{\infty 2} - S_o)*(1-e^{-k_2 t}) + (S_{\infty 3} - S_o)*(1-e^{-k_3 t}) \quad \text{(Eqn. 11)}$$

where $S_o$, $S_t$ are initial and intermediate signals, $S_{\infty 1}$, $S_{\infty 2}$, $S_{\infty 3}$, are final (or end-point) signals (related to $k_1$, $k_2$, $k_3$, respectively), $k_1$, $k_2$, $k_3$, are the observed first-order rate constants, and t is time.

As described above, in some cases, for example, where background predominates the $S_o$ value and when a background correction has been performed on the data before application of the predictive-kinetic method of the present invention, the parallel multiple first order may be expressed as follows:

$$S_t = S'_o + (S_{\infty 1})*(1-e^{-k_1 t}) + (S_{\infty 2})*(1-e^{-k_2 t}) + (S_{\infty 3})*(1-e^{-k_3 t}) \quad \text{(Eqn. 12)}$$

where $S'_o$, is an estimate of initial signal at t=0 (i.e., $S'_o$ corresponds to $S_o$ after correction for the contribution of background signal), $S_t$ is an intermediate signal, $S_{\infty 1}$, $S_{\infty 2}$, $S_{\infty 3}$ are final (or end-point) signals (related to $k_1$, $k_2$, $k_3$ respectively), $k_1$, $k_2$, $k_3$, are the observed first-order rate constants, and t is time. In this example, an estimate of $S_\infty$ may be represented as follows:

$$S_\infty = S_{\infty 1} + S_{\infty 2} + S_{\infty 3} \quad \text{(Eqn. 13A)}$$

$$\Delta S_\infty = (S_{\infty 1} + S_{\infty 2} + S_{\infty 3}) - S'_o \quad \text{(Eqn. 13B)}$$

The relationships shown in Eqn. 13A and Eqn. 13B are applicable to one embodiment of the invention where a "previous" baseline-subtracted current is being used in the modeling. For example, in the case of the GlucoWatch biographer there is a previous cycle "A" during which the biosensor is at the iontophoretic anode, and a present measurement cycle "B" during which the biosensor is at the iontophoretic cathode. The last points (e.g., two points) from the previous cycle "A" are used as a measure of the baseline background current. This baseline value is then subtracted from all the current values obtained in the present measurement cycle "B" before integration of those values. A temperature correction of the previous baseline value may be performed prior to the subtraction step.

Further, empirically it may be determined, for example, that one of the three processes (e.g., $(S_{\infty 1})^*(1-e^{31\ k1t})$) has little correlation with blood glucose amount or concentration. The method then could segregate such a process from the rest of the terms. Accordingly, in this situation, a better fit to the blood glucose data may be represented by the following relationship:

$$S_t = S'_o + (S_{\infty 2})^*(1-e^{-k2t}) + (S_{\infty 3})^*(1-e^{-k3t}) \quad \text{(Eqn. 14A)}$$

In this situation (Eqn. 14) the end-point value would be represented as follows:

$$S_\infty = S_{\infty 2} + S_{\infty 3} \quad \text{(Eqn. 14B)}$$

$$\Delta S_\infty = (S_{\infty 2} + S_{\infty 3}) - S'_o \quad \text{(Eqn. 14C)}$$

In another example, empirically it may be determined a better fit may be obtained while including $S_o$ and eliminating the contribution of one of the processes, that is, a process (e.g., $(S_{\infty 1})^*(1-e^{-k1t})$) has little correlation with blood glucose amount or concentration, for example:

$$S_t = S_o + (S_{\infty 2} - S_o)^*(1-e^{-k2t}) + (S_{\infty 3} - S_o)^*(1-e^{-k3t}) \quad \text{(Eqn. 15A)}$$

where $S_o$, $S_t$ are initial and intermediate signals, respectively, $S_{\infty 2}$, $S_{\infty 3}$, are final (or end-point) signals (related to $k_2$, $k_3$, respectively), $k_2$, $k_3$, are the observed first-order rate constants, and t is time. In this situation (Eqn. 15A) the end-point value would be represented as follows:

$$S_\infty = (S_{\infty 2} + S_{\infty 3}) + S_o \quad \text{(Eqn. 15B)}$$

$$\Delta S_\infty = (S_{\infty 2} + S_{\infty 3}) \quad \text{(Eqn. 15C)}$$

Accordingly, the relationship between each process {e.g., $(S_{\infty 1} - S_o)^*(1-e^{-k1t})$, $(S_{\infty 2} - S_o)^*(1-e^{-k2t})$, and $(S_{\infty 3} - S_o)^*(1-e^{-k3t})$} and an analyte value can be determined statistically by examining the contribution of each process to the total signal, and its correlation to the analyte amount or concentration, for example, the blood glucose measurement. The value of the contribution of that process to the overall determination of the blood glucose measurement may be decided. Alternatively, if the process can be identified with a known process (e.g., mutarotation, Pt oxidation, etc.) the correlation can be determined from first principles.

However, in view of the above, measured current data (i.e., not baseline-subtracted) may be used as the input for the model. In this situation, the background correction would be accomplished by combining the background into the $S_o$ term. Alternatively, the background may be fit into a first or zero order type of behavior if the transient portion of the background is taken into account. Using the measured current data (i.e., not baseline-subtracted) eliminates error due to improper background subtraction arising, for example, from skin permeability differences, incomplete consumption of glucose, as well as, interferences in the anode baseline, sensor noise, or different sensitivities between two sensors in a two sensor system. In a further embodiment, the background may be included as a term in the predictive kinetics, where it is not limited to a first order model, e.g., it could be a zero-order or quadratic-order term. An example of a model including a zero-order term is as follows:

$$S_t = S_o + k_o t + (S_{\infty 1} - S_o)^*(1-e^{-k1t}) + (S_{\infty 2} - S_o)^*(1-e^{-k2t}) + (S_{\infty 3} - S_o)^*(1-e^{-k3t}) \quad \text{(Eqn. 16)}$$

where $k_o$ is a pseudo-zero order rate constant, and the other terms are as described above (e.g., Eqn. 12). Such an approach may be used to resolve the experimental responses into different components, where, for example, one component represents a zero order term.

In yet another embodiment of the present invention, a weighting factor ($\omega_x$) may be used to give different weights to the different processes to improve correlation with blood glucose value. Such weighting factors skew the contribution of the corresponding process to account for the level of contribution of each process to the overall determination of blood glucose value, that is, weighting factors reflect the relative importance of the process with regard to the overall determination. The sum of the weighting factors is typically equal to one (i.e., $\Sigma(\omega_x)=1$, where X is the number of processes). For example, a weighted, three process determination may be represented as follows:

$$S_t = \omega_0 S_o + \omega_1 (S_{\infty 1} - S_o)^*(1-e^{-k1t}) + \omega_2 (S_{\infty 2} - S_o)^*(1-e^{-k2t}) + \omega_3 (S_{\infty 3} - S_o)^*(1-e^{-k3t}) \quad \text{(Eqn. 17)}$$

where $\omega_0$, $\omega_1$, $\omega_2$, and $\omega_3$ are weighting factors and $\Sigma(\omega_0 + \omega_1 + \omega_2 + \omega_3)=1$.

Another approach to baseline correction is to fit a suitable model to the measured current data curve (e.g., i vs. t, where i is current and t is time) and use the predicted, end-point, baseline value to perform background subtraction. In the case of the GlucoWatch biographer (as an example of a two sensor system), iontophoretic extraction takes place into an anodic and a cathodic reservoir, each of which is in contact with a sensor element. The majority of sampled glucose is located in the cathodic reservoir. An anodic detection cycle is performed which results in a response curve comprising data points from which, using the predictive-kinetic methods of the present invention, a baseline, end-point, background value can be predicted. The cathodic detection cycle is then performed. The predicted end-point background value from the anodic cycle may then be used for background subtraction of the data obtained in the cathodic detection cycle (e.g., the predicted end-point background value may be subtracted from each data point of the cathodic detection cycle response curve in order to provide a background corrected response curve for the cathodic detection cycle). This approach compensates for, e.g., incomplete reactions in the anodic half-cycle during operation of the GlucoWatch biographer.

Figure 20B:
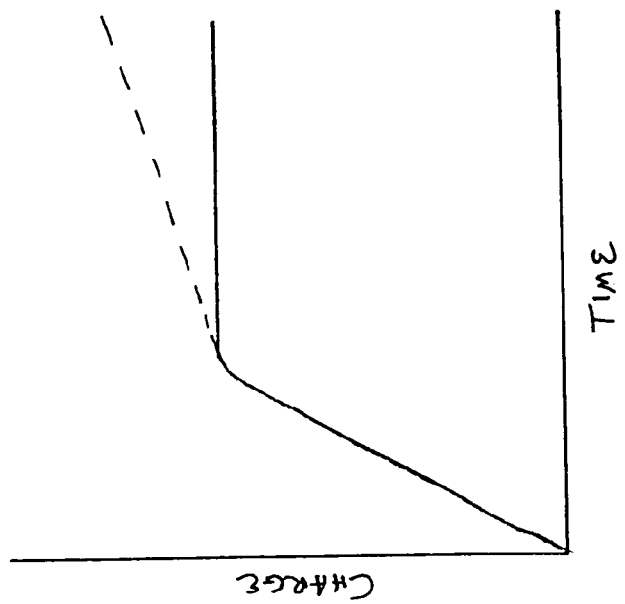
FIGS. 20A and 20B present schematic diagrams of, respectively, negative deviation (dashed line) from an ideal response (solid line), and positive deviation (dashed line) from an ideal response (solid line).
Figure 20A:
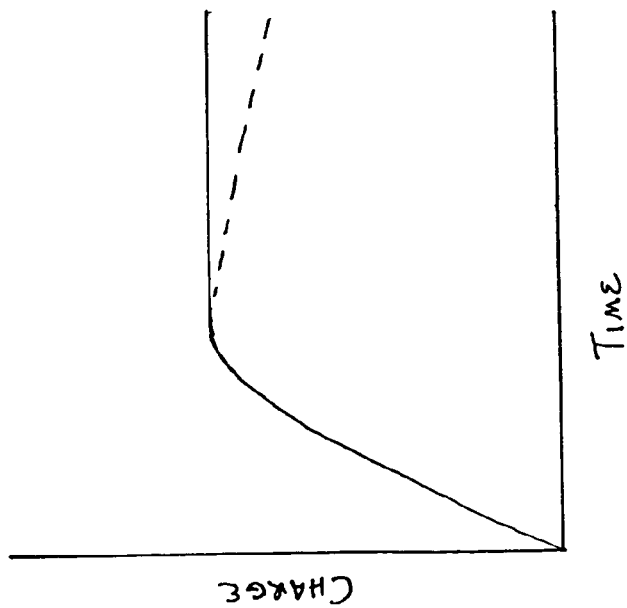

In the current GlucoWatch biographer, a background correction of the cathodic cycle values is performed using an average of at least the last two data points from the current response curve obtained in the anodic cycle measurement which preceded the cathodic cycle. This background correction is performed before integration of the cathodic response (i.e., the background corrected cathodic response data is integrated). In some cases, a negative deviation (FIG. 20A) of the corrected cathodic response is observed when the anodic current value used for the background correction is greater than the cathodic responses near the end of the measurement period (which is typically seven minutes). Conversely, a positive deviation (FIG. 20B) is observed when the anodic current is lower than the cathodic responses.

A final background value (i.e., the anodic or cathodic responses at an infinite time point) can be estimated using a suitable model (e.g., first order, second order, parallel first order, etc.) applied in the predictive-kinetic method of the present invention. This value provides compensation for an incomplete reaction or unstable baseline measured during the anodic or cathodic cycles. Use of this method of background subtraction may provide an integrated response for the cathodic cycle that requires no further treatment. However, application of the predictive-kinetic method of the present invention to the integrated cathodic cycle response curve to predict an end-point analyte-related value may still make a meaningful contribution to accurate prediction of the end-point analyte-related value.

Depending on the data processing method utilized, incomplete reaction of analyte, or an unstable signal, may affect the analytical performance of a device performing frequent measurements, such as the GlucoWatch biographer glucose monitor. For instance, performance is affected when a signal value inconsistent with complete reaction is used to perform background correction. This causes attenuation during the latter period of the response curve, especially for low analyte concentration. One approach to compensate for this is to allow the reaction to go to completion. However, this is may require long measurement time, which is incompatible with providing timely information from a monitoring device, for example, for providing information regarding glucose excursions.

As discussed above, an alternate method is to estimate a signal value consistent with the signal value of the complete reaction by fitting a suitable model to the response. The estimated value is an accurate measure of signal at the completion of reaction and is independent of analyte concentration. This provides a reliable estimate of analyte concentration achieved by subtracting the predicted final background signal from the values of the fitted line of the response curve prior to integration to estimate the area under the response curve. Use of the fitted line rather than raw data provides additional benefit of signal averaging that reduces noise beyond the level attainable by simply integrating the corrected current response. This approach also reduces the influence of systematic noise, such as temperature spikes.

This data processing option was evaluated by fitting a suitable model to the current versus time response of the biographer glucose monitor (Example 6). The model selected was an exponentially decaying signal consisting of two rate processes as shown below:

$$S_t = S_0 + S_1 * e^{-k1*t} + S_2 * e^{-k2*t} + \text{final\_Bkgrd} \qquad \text{Eqn. 20}$$

where $S_0$ is response at t=0, $S_1$ and $S_2$ were the signals consistent with the two processes with pseudo (or apparent) rate constants were $k_1$ and $k_2$, and t was time. Final_bkgrd was the estimated signal response at completion of the reaction. In some cases, such as in the case where there is a large transient background current, $S_0$ may be ignored and Eqn. 20 then becomes:

$$S_t = S_1 * e^{-k1*t} + S_2 * e^{-k2*t} + \text{final\_Bkgrd} \qquad \text{Eqn. 21}$$

Experiments employing Eqn. 21 to estimate end-point background values and resulting corrected data curves are presented and discussed in Example 6. Fits of data (using the predictive-kinetic method of the present invention, for example employing Eqn. 21) to the current versus time response and subsequent data treatment as described herein allows for a reliable estimate of equilibrium value consistent with complete consumption of analyte, for example, glucose. Because this method estimates total analyte consumed, it provides an invaluable tool to examine decline in sensitivity of the response of a monitor to analyte over an extended period.

E. Specialized Algorithms

In yet another aspect of the present invention, prediction of the concentration of an analyte can be accomplished using specialized algorithms, where the specialized algorithms are useful for predictions in particular situations (e.g., particular data sets or ranges of predicted values) and where the algorithm used for performing the calculations is determined based on the situation. In this case a "switch" can be used to employ one algorithm (or group of algorithms) rather than another algorithm (or group of algorithms). For example, in one embodiment of the present invention an algorithm is used to determine if enough data has been collected to obtain accurate measurements using the predictive-kinetic method of the present invention. First, current data is collected (e.g., at least three signal values in the kinetic range). A rate constant (k) is estimated for a first order model by plotting the natural log of signal ($S_t - S_o$) versus time, where the slope of the resulting line corresponds to an estimate of k. The half-life of the process is then estimated using, for example, $t_{1/2} = \ln 2 / k$. A "switch" in the algorithm is used as follows: (a) if three times the resulting value for the half-life is less than what has empirically been determined to be the average optimal measurement time, then that measurement time is considered to be sufficient and the data is employed by the predictive-kinetic method to estimate an end-point value. However, if (b) the three times resulting value for the half-life is greater than the average optimal measurement time, then the biographer is instructed by an algorithm to continue its measurement cycle until three half lives of the signal (or a finite cut-off point) is achieved, before proceeding to the predictive-kinetic method to estimate an end-point value.

Initial estimates of parameters that vary significantly from the real values (i.e., measured values) can cause problems of non-convergence and in some cases require many iterations to achieve convergence. One solution to this problem is to use empirical methods to compute initial estimates, such as, linear regression to estimate a rate constant from a plot of $\ln(S_t - S_o)$ vs t. This method is useful when the range of the data being used generally follows first order response; otherwise inaccurate estimate of the rate constant can result.

For cases where the responses are non-first order, a different approach, such as Guggenheim method (Guggenheim, E. A. Philos. Mag. J. Sci.; 1926, 2, 538) may be employed. The Guggenheim method assumes no knowledge of the response profile and uses an algorithm to estimate the rate constant. In the Guggenheim method, several pairs of responses, $S_i$ and $S_j$ are measured, with each pair being separated by the same fixed time interval, t. Then $\ln(S_i - S_j)$ vs $t_1$ is plotted to obtain a linear plot with intercept on the Y-axis equal to $\ln S_o$, from which $S_o$ is computed. The form of the equation used in the process is as follows:

$$\ln(S_1 - S_n) = -kt_1 + \ln[(S_o - S_{ss})(1 - e^{-k\Delta t})] \qquad \text{(Eqn. 18)}$$

where $S_1$ is the response measured at the first point in time, $t_1$, and $S_n$ is the response measured at the last point in time, $t_n$, k is the slope of the line, $S_{ss}$ is the steady-state response.

The method of partial sums (see, e.g., Cornell, R. G. Biometrics (1962) 18:104-113) may also be employed to provide reliable values of initial estimates of the rate constant without prior knowledge of response at $t=0$ ($S_o$) or time t ($S_t$).

In most cases, either the Guggenheim or partial sum method produces only one distinct value for the rate constant, then a second rate constant, for example for a two process parallel first order model, may be obtained using the first rate constant. One approach to accomplish this is to multiply the first rate constant value by a selected factor.

Once accurate initial estimates of the rate constants are obtained, then initial values of other parameters may then be computed by multiple regression with the equation below for a parallel first order model, for example, as follows:

$$S_t = S_o + S_{\infty,1}[1-\exp(-k_1^\circ t)] + S_{\infty,2}[1-\exp(-k_2^\circ t)] \quad \text{(Eqn. 19)}$$

where $k_1^\circ$ and $k_2^\circ$ are the computed initial estimates of rate constants for a parallel first order model. Other parameters in this equation have been described above. Finally these initial estimates are used with, for example, Eqn. 6A to predict best-fit values of the final responses.

Further, different models employed in the predictive-kinetic method of the present invention may be used under different circumstances. In this case, a more global algorithm can be the switch used to selected one of several different algorithms (e.g., switching between a first order model and a parallel multiple first order model). In one embodiment such a global algorithm may be used to determine a preliminary blood glucose value. The blood glucose value is determined, by the algorithm, to fall into one of three ranges (for example, low, normal, and high). For each range there is an separate predictive-kinetic algorithm that optimizes the prediction for values in the particular range.

Specialized algorithms may be developed to be used in different parts of a range of analyte signal spectrum or other input values (e.g., for all parameters used in the prediction). A global algorithm can be used to decide which region of the spectrum the analyte signal is in, and then the global algorithm switches the data to the appropriate specialized algorithm. Further, there can be multiple levels of specialized switching (which can be graphically represented, for instance, by branched tree diagrams).

Experimental

The following examples are put forth so as to provide those of ordinary skill in the art with a complete disclosure and description of how to make and use the devices, methods, and formulae of the present invention, and are not intended to limit the scope of what the inventor regards as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Preliminary Studies

The data was collected at room temperature using the GlucoWatch biographer. In these studies, the biosensor was assembled and preconditioned for one hour. Ten microliters of glucose solution of known concentration was then deposited on the hydrogel. The electrode response to the glucose was monitored for 60 minutes. The current responses were then transferred to a computer for data processing.

Figure 3:
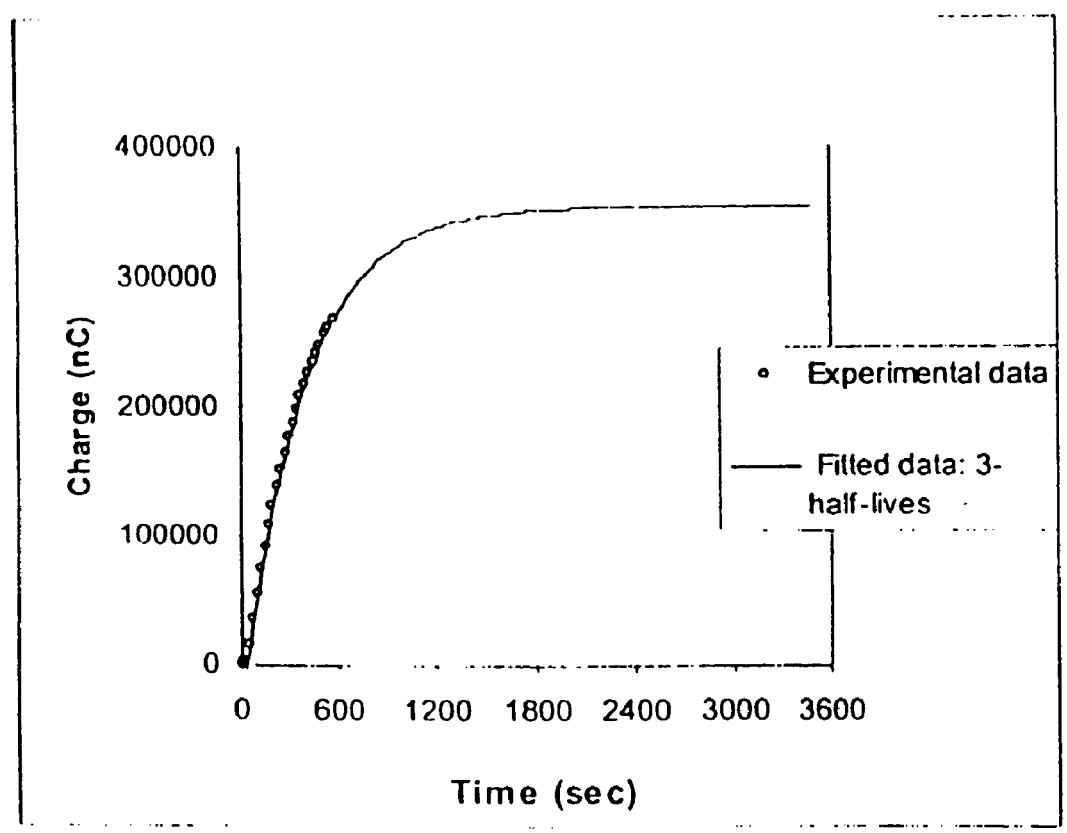
FIG. 3 shows experimental and fitted data for charge versus time responses using a 200 micromolar solution of glucose.
Figure 4:
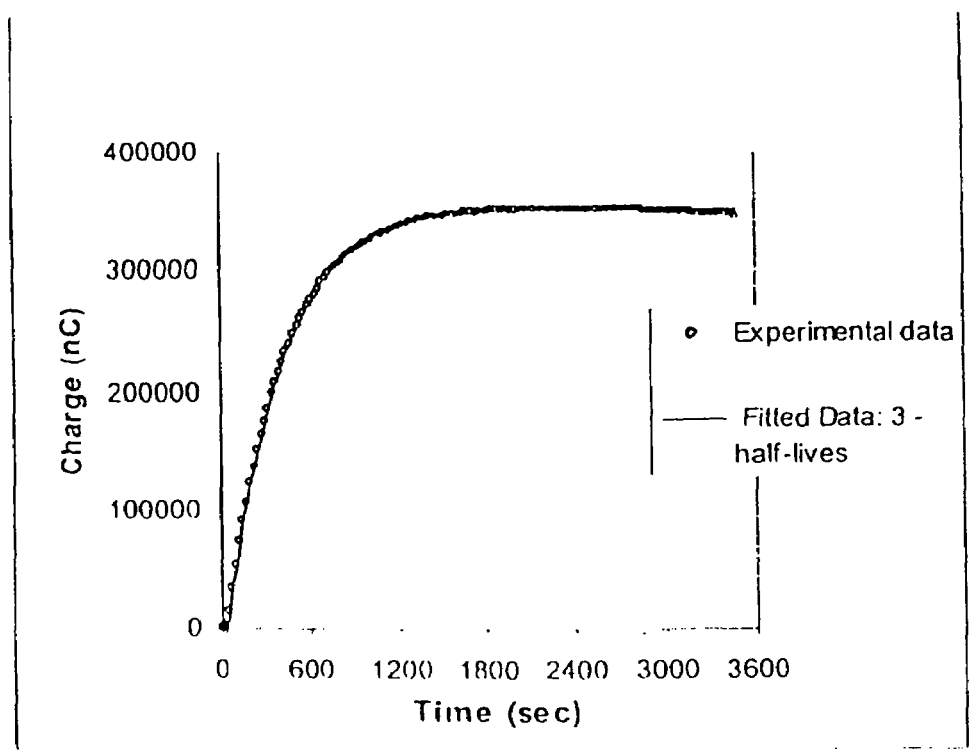
FIG. 4 shows experimental and fitted data for charge versus time responses using a 200 micromolar solution of glucose, where the experimental data was monitored to completion.

In FIGS. 3 and 4, the points are experimental data for response of the biographer to 200 μmol/L glucose and the solid curve is fit to the data using the first-order model:

$$S_t = S_\infty - (S_\infty - S_o)e^{-kt} \quad \text{(Eqn. 1)}$$

where $S_o$, $S_t$, and $S_\infty$ are initial, intermediate, and final signals, k and t are the first-order rate constant and time, respectively. The experimental response was obtained by first applying preconditioning potentials at 0.77V vs. Ag/AgCl for 10 min, followed by a step down to 0.42V vs. Ag/AgCl for 50 min. At the end of the 60 min preconditioning period, 10 μL of the 200 μmol/L glucose solution was deposited on the hydrogel and the response was monitored to completion. The current measured after the solution was deposited was integrated and is shown in FIGS. 3 and 4 as charge vs. time response.

The first-order model was fit only to the data during the first three half-lives (open circles) of the process. By extrapolating the fit backward to $t=0$ and forward to $t \geq 10\, t_{1/2}$ it is possible to obtain predicted values of the initial and final values of the signal $S_o$ and $S_\infty$, respectively. Agreement between computed and measured results is illustrated in FIG. 4 which contains more experimental data points near equilibrium. By using the predicted values, it is possible to compute the signal change, $\Delta S = S_\infty - S_o$, that would have been measured had the process been monitored from $t=0$ to equilibrium or completion. This predicted change varies linearly with glucose concentration.

Figure 5:
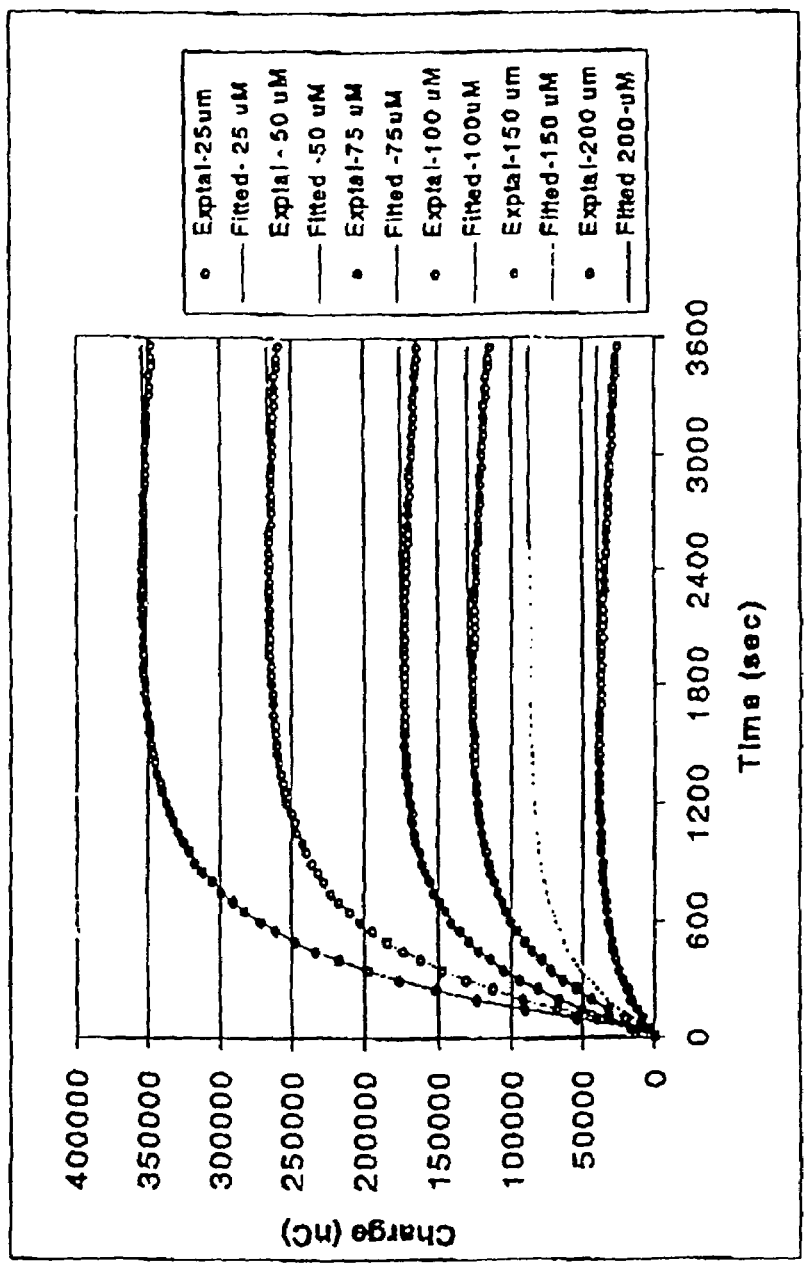
FIG. 5 shows charge versus time responses for different glucose concentrations where the fitted lines were calculated using three half lives of the signal.

Further, charge versus time responses for different glucose concentrations were also evaluated. Glucose solutions of different concentrations were evaluated as described above. The data are presented in FIG. 5. In the figure, dots represent data points and the lines the fitted curves using Eqn. 1 and an error minimization protocol. The fitted lines were calculated using three half-lives of the signal. The results demonstrate the high correlation of the predictive-kinetic method of the present invention to glucose concentration or amount in the sample as detected by the biographer.

These results demonstrate the ability of the predictive-kinetic method of the present invention to accurately estimate glucose concentration or amount based on the data provided by the biographer.

EXAMPLE 2

Further Modeling Studies

Figure 6:
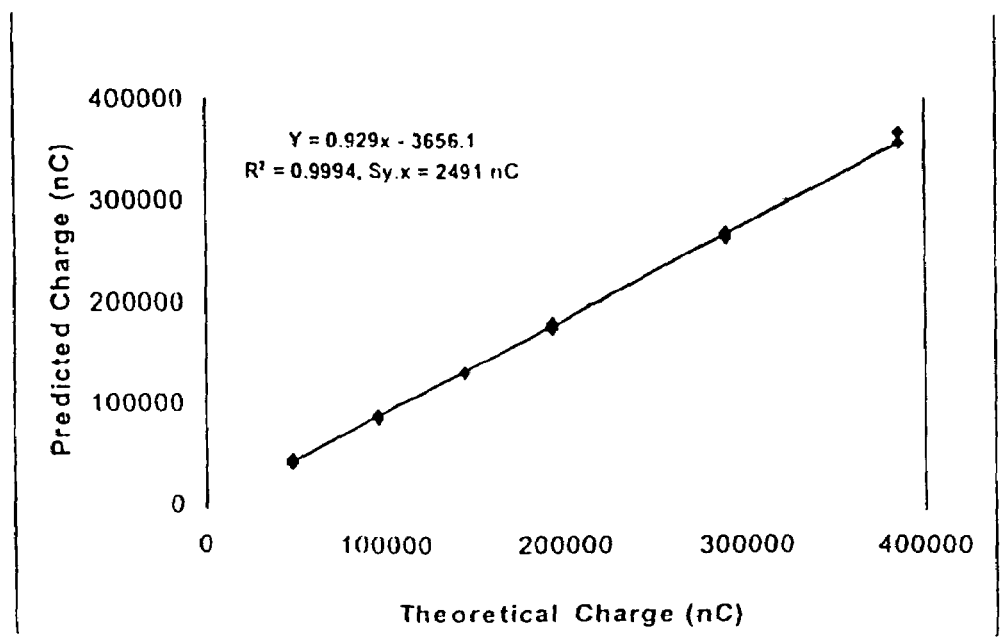
FIG. 6 presents a plot of predicted charge at three half lives of the signal versus the theoretical charge based on the glucose concentration used.

In this study the responses of the biographer to different concentrations of glucose (25 to 200 μmol/L) was monitored using the procedure described in Example 1. The concentration range covered the extracted glucose values, as determined using a biographer, found in patients with diabetes. The experiment was performed at room temperature using sensors of moderate sensitivity. There were six replicate measurements at each concentration. The first-order model was fitted to the integrated data using several half-lives. The first half-life was 250 secs. FIG. 6 presents a plot of the predicted charge, obtained with the predictive-kinetic method, vs. the theoretical charge.

During the measurement of glucose, the biosensor current is integrated as a function of time. The integral of an electrical current is an electrical charge ($Q = I \times t$). Because the total amount of glucose added to the biosensor in this experiment and the number of electrons released during the electrochemical reaction (2 per glucose molecule) were known, the theoretical charge was calculated by the Faraday equation:

$$Q = N \times n \times F \times 10$$

where N=concentration of glucose, μmol/L deposited on the hydrogel; n=number of electrons released per mole of glucose; F=96,500 C/mole, i.e., Faraday's constant; and 10 equals the volume of glucose, μl.

FIG. 6 shows a plot of predicted versus theoretical charge and the slope value which represents the extent of recovery of the glucose concentration deposited on the hydrogel was >93% (this value was obtained from the slope of a plot of predicted charge vs. theoretical charge shown in FIG. 6, where the slope was approximately 0.929 or approximately 93%). When the theoretical charge was achieved, it was termed 100% recovery of the analyte, and was considered the end-point of the reaction. Theoretical charge is plotted on the x-axis in FIG. 6. The end-point charge predicted by the predictive-kinetic model using three half-lives of the response data, are plotted on the y-axis.

For the 200 μmol/L sample, average of charge estimated by the predictive-kinetic method was 363,930 nC compared to an expected value of 386,000 nC, >or 94% which is close to the average of 93% determined from the slope of the line in FIG. 6. This shows that the predictive-kinetic method can, on average, estimate 93% of the measurement objective consistent with complete glucose consumption. The predictive-kinetic method also gave results with low imprecision ($S_{y,x}$=2491 nC).

Results for other fitting ranges are shown in Table 1. These values were obtained from a plot of predicted charge versus concentration (micromole per liter). The slope value is given in nC/μmole/L.

TABLE 1

| Method | Slope (nC/μmol/L) | In-tercept (nC) | $R^2$ | Sy.x (nC) | Pooled S.D (nC) | Variance Ratio |
|---|---|---|---|---|---|---|
| First-Order: | | | | | | |
| 1st half life | 2315 | −19697 | 0.9442 | 31167 | 32620 | 0.91 |
| 2nd half life | 1829 | −4313 | 0.9975 | 5242 | 5355 | 0.96 |
| 3rd half life | 1785 | −3131 | 0.9993 | 2768 | 2894 | 0.91 |
| 4th half life | 1777 | −2968 | 0.9996 | 2064 | 2193 | 0.89 |
| 8th half life | 1791 | −5127 | 0.9996 | 2169 | 2233 | 0.94 |

The values in the slope column show that data using three half-lives provide a reliable estimate of the end-point charge. Also included are the pooled standard deviation and the variance ratios estimated from the equation given below.

$$\text{Variance ratio} = S^2_{y,x} / SD^2_{pooled}$$

The variance ratio was used to verify that the first-order model used was a valid option for this data set. The $F_{table}$ at 95% Confidence Interval is 2.78 and since the variance ratios are all less than this value, it confirmed that the fit of the first-order model to the data was valid.

Although the first order model data fits the empirical data well, other empirical models are available (including a parallel multiple first order and an n-th order model) which do not require knowledge of the reaction order and which can provide accurate predictions. For example, analyses of these data using alternative models (e.g., a combined zero order and first order model, as well as, a diffusion-limited flux model) also provided good fit of the data to the models.

EXAMPLE 3

First Order Versus Parallel-First Order for Fitting Clinical Data

Modeling of clinical data obtained from patients with diabetes demonstrated that the parallel multiple first order model fits clinical signal from the biographer's biosensor more accurately than first order model. This is, at least in part, because the biographer is used in such a fashion that involves at least two rate processes—initial reaction at the electrode and at least one parallel reaction, in this case where the second parallel reaction may be mutarotation and diffusion dependent. During the three-minute extraction cycle used by the biographer, glucose accumulates in the hydrogel near the reactive face of the biosensor, and once the potential is applied a large current response is observed. This gives rise to the first rate process. Further rate processes can be due to other factors such as mutarotation and diffusion of glucose through the hydrogel. These further processes are typically much slower processes. In the present case, the second rate process considered primarily resulted from diffusion.

Figure 7:
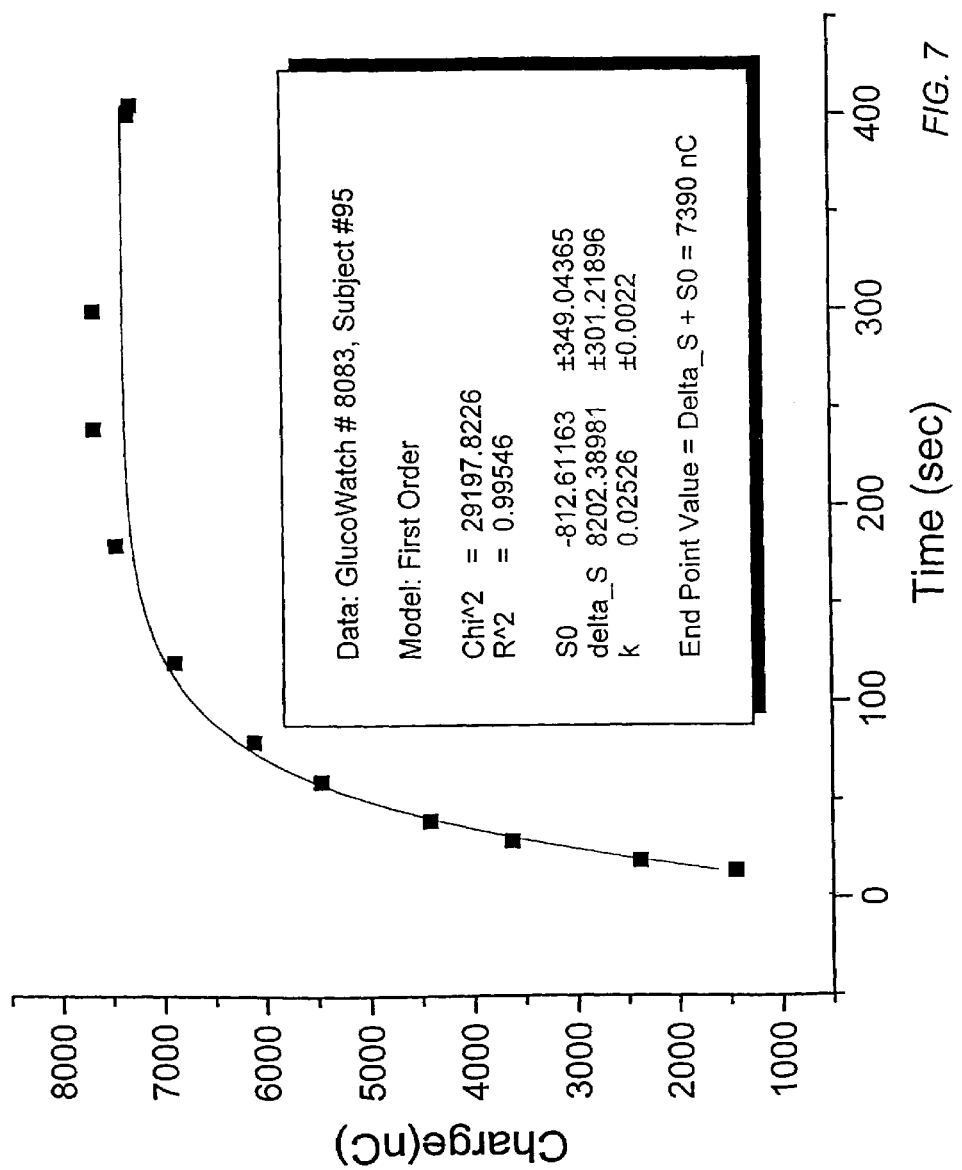
FIG. 7 presents a plot of a typical fit of a first order model to signal from a sensor device.
Figure 8:
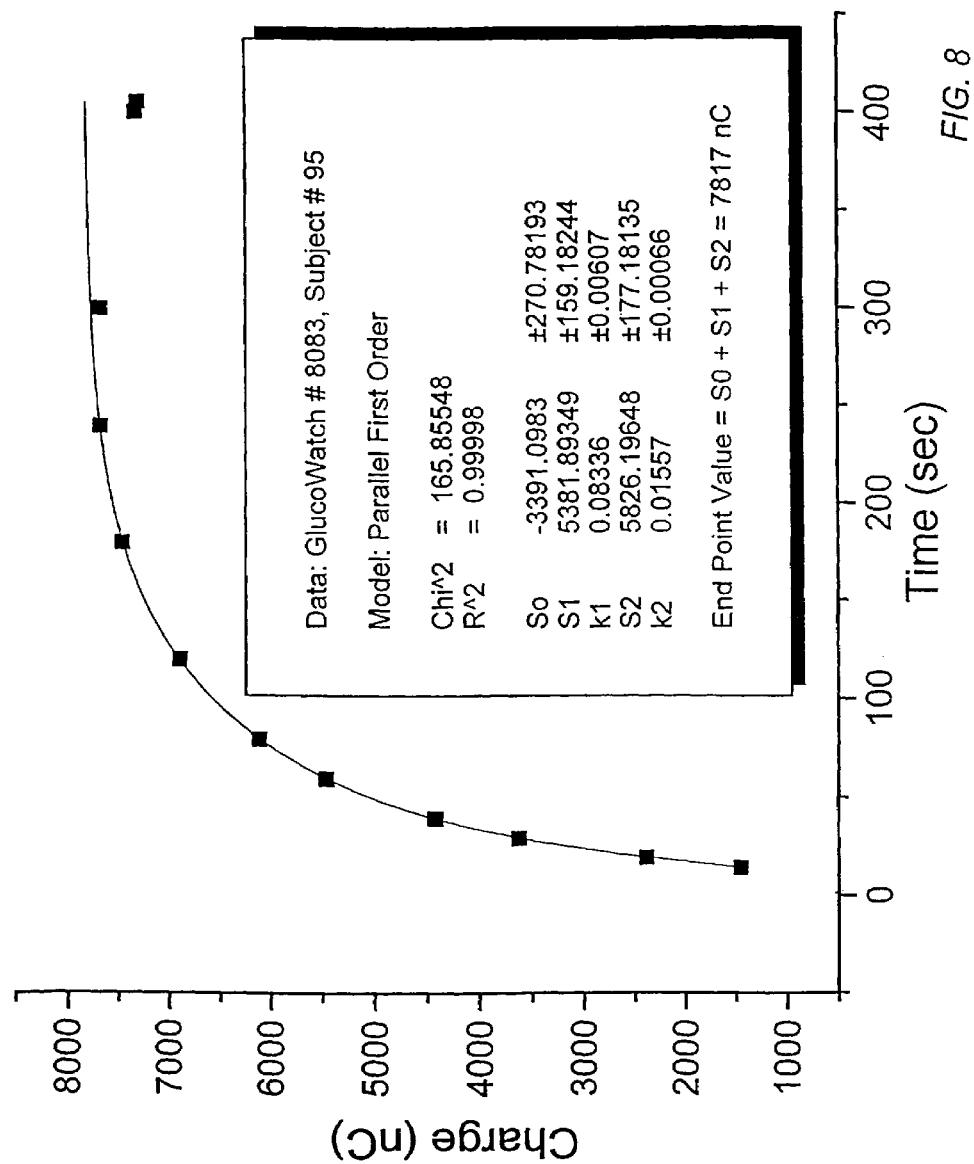
FIG. 8 presents a plot of a typical fit of a parallel multiple first order model to signal from a sensor device.

The data was collected at room temperature using the GlucoWatch biographer worn by a non-diabetic test subject. The data presented in FIGS. 7 and 8 show typical fits of models to signals (i.e., a single charge measurement predicted over a three minute time period presented in nC) obtained using the biographer. The fits are of a first order model (Eqn. 1 above; to data shown in FIG. 7) and a parallel multiple first order model (Eqn. 10 above; to data shown in FIG. 8). The improvement in the fit using the parallel-first order model is shown by lower $\chi^2$ value (165) and higher value (29197) for the First Order model (see legends in FIGS. 8 and 7, respectively). Further, the ratio of k1 to k2 may be used to determine the quality of the fit. For example, in the present analysis, based on bench-top data the ratio was expected to be about 9±2. If the fit of a model (Eqn. 21) to a response gives a ratio significantly different from 9±2 it makes the quality of that particular response reading questionable and, accordingly, may be eliminated as an erroneous reading.

Figure 9:
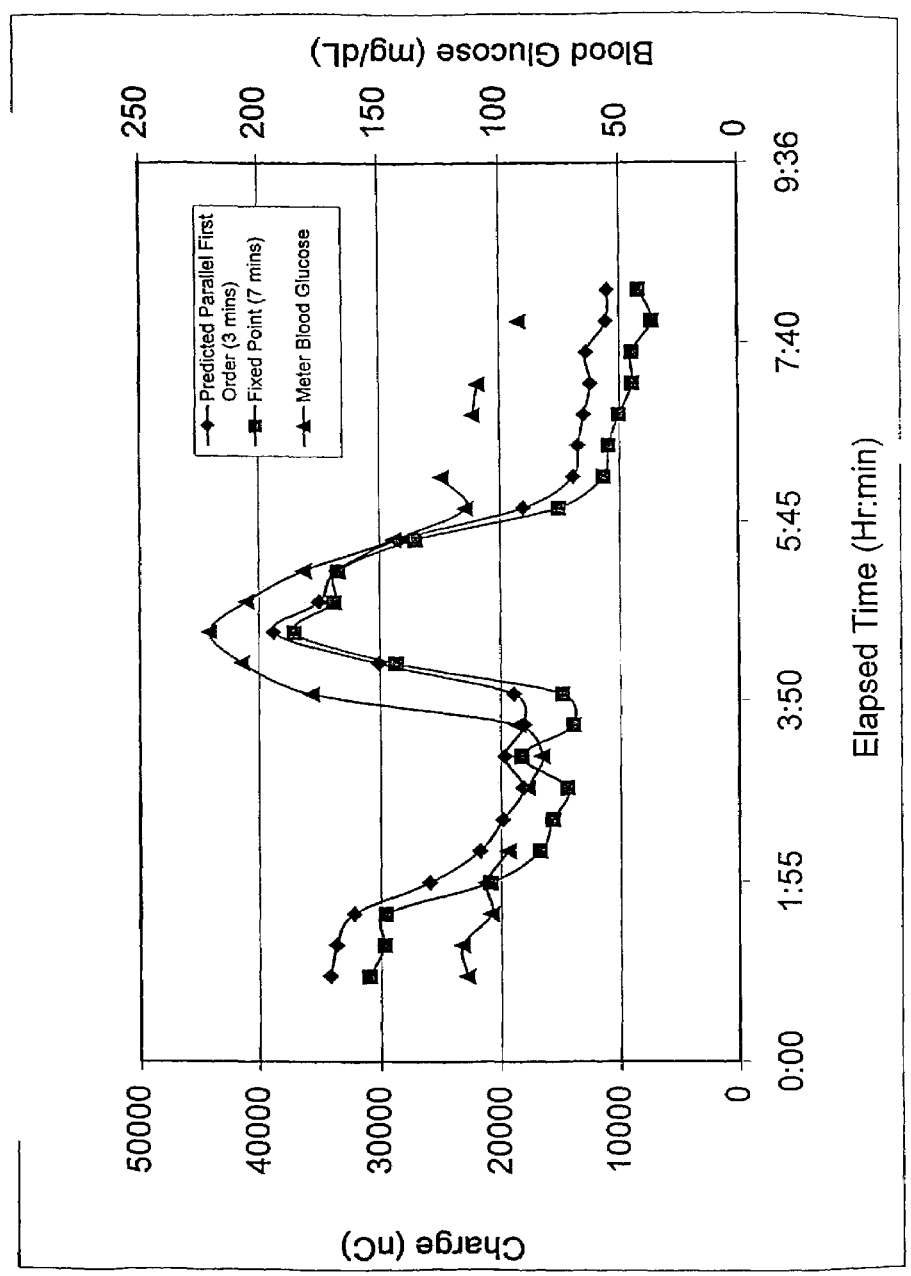
FIG. 9 presents a plot of typical measurements for a non-diabetic subject using data from a sensor device (employing predicted charge values based on a parallel multiple first order model fit to the data and a fixed point method), as well as blood glucose measured by a conventional, invasive meter.

After 3 hours of data were collected, the subject took a large dose of oral glucose. The data from the experiment is presented in FIG. 9. In the figure, triangles show the values obtained using a standard finger prick method and conventional meter to determine blood glucose, the scale for this measurement is the Blood Glucose (secondary Y-axis); squares show data gathered using the biographer employing a fixed point measurement method (the fixed point determination being made after 7 minutes of signal measurement), the scale for this measurement is presented on the Charge axis; and diamonds show data gathered using the biographer employing a three minute measurement and the predictive-kinetic method of the present invention using a parallel multiple first order model (Eqn. 10, above), the scale for this measurement is presented on the Charge axis. The plots in FIG. 9 present results for all extraction/measurement cycles during an eight-hour test.

The signals predicted by the parallel-first order and the fixed point methods both tracked with the meter-estimated blood; however, the signals predicted by the parallel multiple first order used only three minutes of the collected data for the prediction, as compared to 7 minutes used for the fixed time method.

Figure 10:
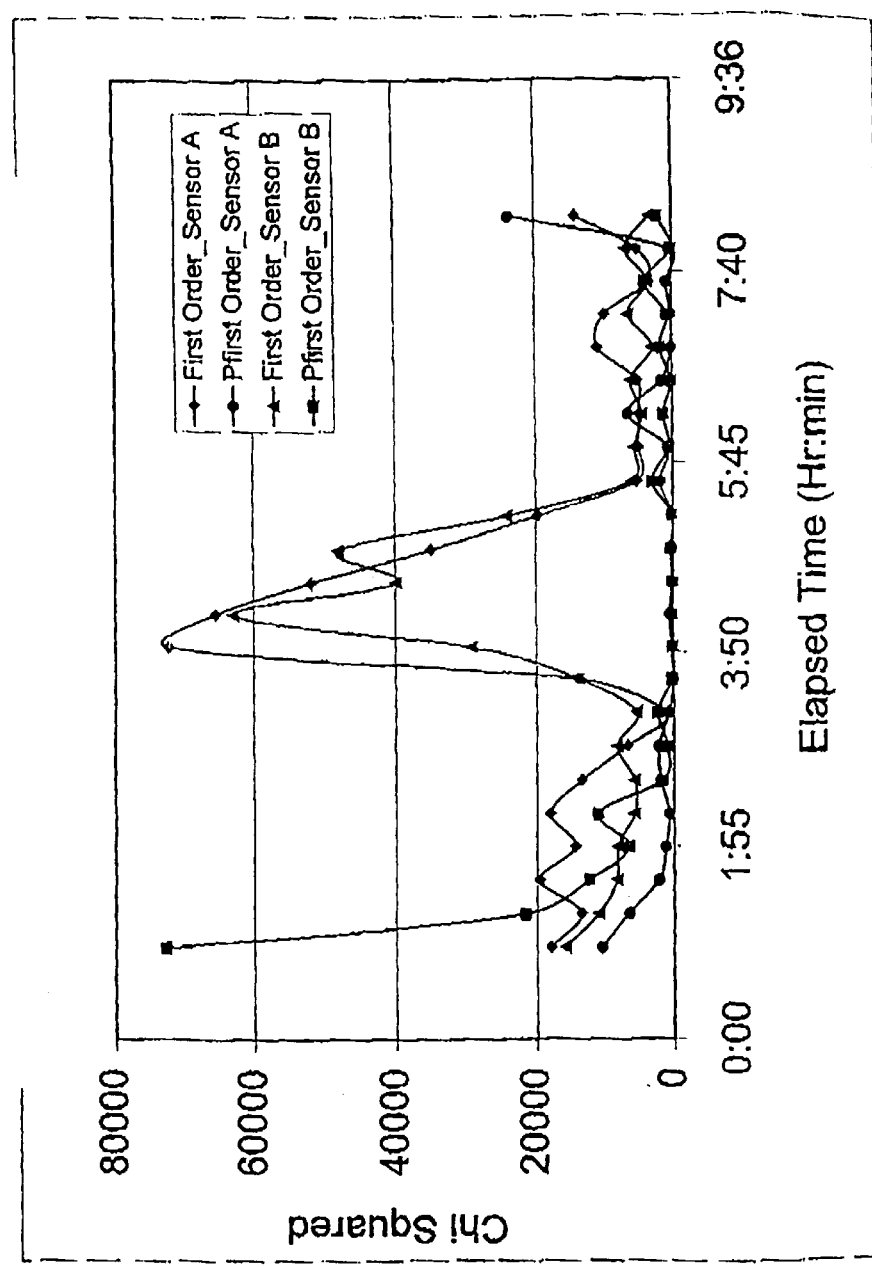
FIG. 10 presents a plot of the efficiency of error minimization (chi-square) using first order and parallel multiple first order models to fit the data. The parallel multiple first-order model better fits the response data and is not affected by analyte concentration. The first-order model best fit the response data when analyte concentration was low. However, at high analyte concentration (e.g., between 3:00 and 5:00 hours elapsed time in FIG. 10) the fit to the response data using the first-order model had higher associated error, as shown by the high chi-square values in this region.

Finally, a plot of chi-square versus elapsed time for all cycles clearly showed that both first order and parallel multiple first order can fit the time-dependent responses from a test subject for normal glucose levels at lower levels of blood glucose (FIG. 10). In the figure, the data is broken down into measurements at the first and second sensors (i.e., sensors A and B) employed by the biographer. Using the biographer, a complete measurement cycle is typically as follows. Analyte is extracted from the test subject into a first hydrogel using a three minute iontophoretic extraction, followed by the sensing (or measurement) period for that hydrogel, i.e., determination of current associated with the amount or concentration of analyte present in the hydrogel. This cycle is repeated employing a second hydrogel. Accordingly, a "complete" measurement cycle includes the signal data from both hydrogels.

However, at higher glucose levels, the first-order did not provide as reliable estimates of the end point values as the parallel multiple first order which gave more consistent values (FIG. 10, time period from approximately three to five hours). The increase in chi-square values for fits with the first order coincided with ingestion of an oral glucose drink by the test subjects at about three hours into the study. This increase in glucose levels affected the results of first order model while the parallel multiple first order model continued to provide reliable estimates of the end point values as shown by low and constant chi-square values throughout the study period.

EXAMPLE 4

Variable Dependency Study

Temperature was selected as a variable to demonstrate the reduced dependency of the predictive-kinetic method on measurement variables. This variable was selected because it affects the rate of mutarotation as well as the rate of physical processes such as diffusion of glucose through a hydrogel (Kurnik R. T., et al., Journal of the Electrochemical Society 145 (1998) 4119-4125). Data were collected with the biographer at 21° C. and 32° C.

The equilibrium charges at each temperature were estimated using the predictive-kinetic method by fitting the first-order model to the charge vs. time responses. The data range used was three half-lives. The data showed that the same equilibrium charge was predicted for both temperatures.

Table 2 below contains average results of the study. Four replicate measurements were made at each temperature. The effectiveness of the predictive-kinetic approach to deal with temperature variation was demonstrated by fitting a first-order model to data collected at two measurement temperatures (21° C. and 32° C.) for 200 µmol/L glucose. Even though the pseudo-first order rate constant increased from 2.3 to $4.4 \times 10^{-1}$ (see Table 2 below), the predicted end-point signal only increased by 6%. By comparison, non-end point methods, such as, integrated signals at a fixed-time of 10 minutes, showed an increase of 26% in the response to the change 11° C. Clearly, the predictive-kinetic method gave consistent results regardless of the measurement temperature. The percent change observed with the predictive-kinetic method was negligible. Another important observation was that, regardless of the rate constant, similar equilibrium values were computed using the predictive-kinetic method. This is shown by the percent recoveries of 95% and 100% estimated at the two temperatures using the predictive-kinetic method.

TABLE 2

|  | 21° C. | 32° C. |
| --- | --- | --- |
| Ave (nC) | 367700 | 391435 |
| Std. Dev | 17196 | 5967 |
| % CV | 4.8 | 1.5 |
| % Recovery | 95 | 101 |
| % Change/° C. | — | 0.6 |
| Ave Rate Constant ($10^{-3}$, $sec^{-1}$) | 2.3 | 4.4 |

EXAMPLE 5

Compensation of Declining Signal by the Predictive-Kinetic Method

Response curves were established for the last four hours of (i) a glucose monitor employing a Pt/C electrode and the predictive-kinetic method, and (ii) a glucose monitor employing a Pt/C electrode and a fixed-time concentration determination method (fixed integral measurement). The predictive-kinetic method was based on a parallel multiple first order response (see above, Eqn. 6A) using three minutes of signal measurement per data point. The fixed time determination was based on seven minutes of signal measurement per data point. The response curves are presented in FIG. 11. Also in FIG. 11 data for blood glucose amounts as determined using a OneTouch® (Johnson & Johnson, New Brunswick, N.J.) device are presented in solid triangles with the reference axis being the right vertical axis.

Figure 11:
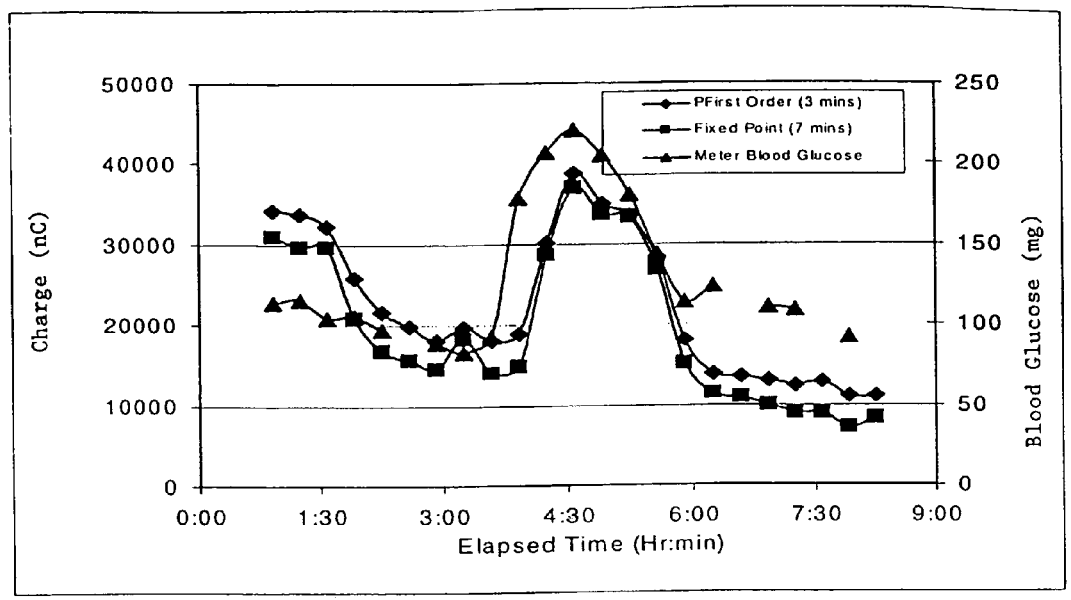
FIG. 11 presents response curves for typical measurements from a non-diabetic subject using two data-processing methods, one using a predictive-kinetic method to determine glucose signal related charge (closed diamonds) and the second using a fixed point method to determine glucose signal related charge (closed squares). Data for blood glucose amounts as determined using a OneTouch® (Johnson & Johnson, New Brunswick, N.J.) device are presented in solid triangles with the reference axis being the right vertical axis.
Figure 12:
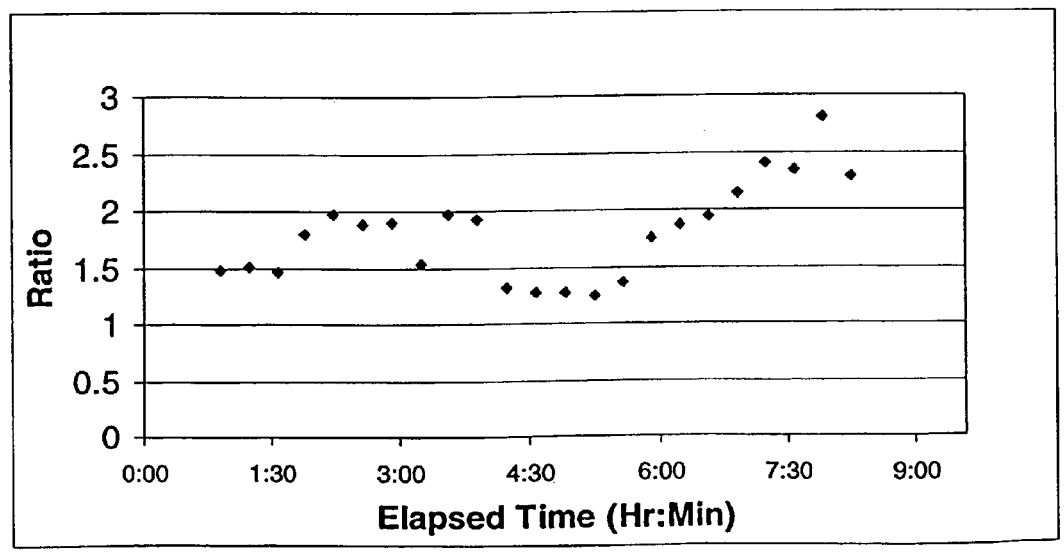
FIG. 12 presents the ratio of predicted versus fixed-time point signal methods based on the data presented in FIG. 11.

The data presented in FIG. 11 clearly show an apparent decline in the values obtained by the fixed-point method. The values predicted by the kinetic model are higher for the same region. This difference in decay can be illustrated by plotting a ratio of the predicted values to the fixed-point data. The ratios of the values in FIG. 11 are plotted as a function of elapsed time in the FIG. 12. Values greater than one would indicate apparent compensation of the decline in signal by the predictive-kinetic method compared to the non-equilibrium, fixed-point method. The data presented in FIG. 12 clearly show that during the nine-hour study, the magnitude of the predicted values is consistently higher than that of the fixed-point method. The last four hours also showed an increase in the ratios consistent with a more rapid decline in the responses estimated by the fixed-point method. Hence, the predictive-kinetic approach has the potential to measure essentially all glucose extracted into the hydrogel, regardless of the sensor sensitivity, thereby compensating for the signal decline seen with a fixed integral measurement.

EXAMPLE 6

Compensation of Incomplete Reaction by Predicting Signal at Completion

The data collection sequence used here was similar to that used with human subjects wearing the device. The sensors contained in the biographer glucose monitor were preconditioned sequentially at 0.77 and 0.42 V versus Ag/AgCl reference electrode (i.e., potential is applied between the working electrode and a reference electrode (Ag/AgCl)) for 10 minutes, respectively. Subsequent data collection was performed at 0.42V. Multiple data points were collected from both sensors over a 7 minute time period followed by a 3 minute off-period between measurements. Data points were obtained from each of two sensors by taking a time point measurement on one sensor followed by a time point measurement on the second sensor and repeating this switching back and forth over the 7 minute period. All measurements were performed at 32° C. temperature. To simulate glucose extraction, 3 μl of glucose of known concentration was deposited (two hours after the start of preconditioning) on each sensor attached to the biographer glucose monitor in the middle of each 3 minute off-period. Sample addition was repeated two times, at four and six-hour intervals, resulting in six replicate measurements for a single glucose concentration. A similar procedure was performed in a random fashion for the following glucose concentration: 0.00267, 0.00888, 0.015, 0.030, 0.0450, and 0.060 mM. Data were transferred to a computer for processing.

Typical time dependent responses of the biographer glucose monitor to different concentrations of glucose are shown in FIG. 14. The magnitude of the responses curves correlated to the concentration of glucose samples. In standard practice, the values of the signals at 405 seconds, which were inconsistent with values at complete reaction, were used to perform a point-by-point subtraction of the time dependent response. Integration of the signal using this approach is shown in FIG. 15. Though not apparent in FIG. 15, simply using measured current value at 405 seconds for background subtraction resulted in over correction, as shown by non-equilibrium charge at latter time points.

Fits of curves, based on applying the predictive-kinetic method of the present invention as represented in the embodiment of Eqn. 19, to the responses in FIG. 15 are shown in FIG. 16. Fitting Eqn. 19 to the charge versus time response (FIG. 16) compensated, to some extent, for the over correction seen by simply using measured current value at 405 seconds for background subtraction in FIG. 15.

FIG. 17 presents the data obtained from typical fits using Eqn. 21 to fit the response data presented in FIG. 14.

$$S_t = S_1 * e^{-k1*t} + S_2 * e^{-k2*t} + \text{final\_Bkgrd} \qquad \text{Eqn. 21}$$

Even though data was collected for 405 seconds, the fitted lines were extended to 1600 seconds to illustrate reliable estimate of a true current at complete consumption of the glucose (i.e., end-point). FIG. 18 presents integrated responses from fitted current after background correction using the predicted, end-point, background current that was obtained in FIG. 17. The profiles of charge values clearly demonstrate that a constant signal was achieved after 800 seconds for all concentrations using this data processing method.

For all the concentrations investigated, the predicted background current determined by using Eqn. 21, was lower than or equal to the measured value at 405 seconds. A plot of background current versus concentration is presented in FIG. 19. In the figure, measured current at 405 seconds showed a correlation with glucose concentration (y=380.47x+68.25; $r^2$=0.5715), whereas predicted current was independent of glucose concentration (y=37.205x+67.53; $r^2$=0.0106). These results demonstrated incomplete consumption as a function of the amount of glucose deposited on the sensors attached to the biographer glucose monitor, which in turn affected any data processing option that used the measured signal at 405 seconds for background correction. However, use of the predicted current at completion for background correction resulted in higher sensitivity for the same glucose concentration and improved the performance of the biographer glucose monitor.

A demonstration of higher sensitivity estimated by using predicted current from Eqn. 21 and integration of fitted response curve after background correction with the resulting predicted background value was shown by estimating the slope of a calibration curve between experimental versus theoretical charge. The theoretical charge for each concentration of glucose was computed using the method presented in Example 2. The slope obtained using this method and imprecision for this method were compared to other data processing approaches and results are shown in Table 3.

TABLE 3

Linearity Studies
Comparison of Methods for Fit of Models to Biographer Response

| Method | Fit Range (sec) | Slope | Intercept (nC) | $R^2$ | $S_{y,x}$ (nC) | Pooled Standard Deviation (SD) (nC) | Variance Ratio | Model Fidelity**** |
|---|---|---|---|---|---|---|---|---|
| Fixed Time at 405 seconds* | (not applicable) | 0.4866 | 2088 | 0.9945 | 691 | 566 | 1.49 | OK |
| Eqn. 19** | 15-180 | 0.5349 | 2088 | 0.9957 | 676 | 538 | 1.58 | OK |
| Eqn. 21*** | 30-405 | 0.7485 | 2849 | 0.9936 | 1158 | 1078 | 1.15 | OK |

*Measured charge at 405 seconds after correction using current at 405 seconds (as background) and integration.
**Fitted to charge versus time response using Eqn. 19 after correction using current at 405 seconds (as background) and integration.
***Fitted to current versus time response (Eqn. 21) to predict current at completion of the reaction. Predicted current at the completion of the reaction (i.e., final background) was used for background subtraction of the predicted current response curve prior to integration.
****Comparison of Variance Ratio to the F value at 95% CI(5.25) = 2.76. If Variance Ratio is less than 2.76 the Model Validity is indicated as OK.
In Table 3, F-ratio = Var. Ratio = $SD^2_{between\ group}/SD^2_{within\ group}$ where Var. Ratio = $S_{y,x}^2$/Pooled $SD^2$.

Fixed time method represented use of the value at 405 seconds (FIG. 14) to perform background subtraction and integration of corrected current. The charge value at 405 seconds represented the measured signal (FIG. 15). The results presented in Table 3 clearly demonstrated that the fit of current versus time curves, using Eqn. 21 to fit over the range of values from 30 to 405 seconds (FIG. 17), to predict signal at completion of the reaction, and integration of the fitted line after background subtraction using the predicted value (FIG. 18) represented a reliable and robust data processing method. The method employing end-point background values estimated using Eqn. 21 gave the largest slope (0.75) and showed that 75% of deposited glucose was accounted for by this method. Using Eqn.19 to fit integrated charge over 180 seconds (FIG. 16), after correction with background signal measured at 405 seconds, accounted for 53% of the glucose sample. The fixed time method only accounted for about 49% of the glucose sample.

The variance ratios for each method were estimated and the results are shown in Table 3. Analysis of these values using an F-test showed that the three models are valid for estimating responses of the biographer glucose monitor to glucose (i.e., computed F-ratio for the three models are less than the F-value at 95% confidence interval, i.e., less than 2.76). More importantly, fits of Eqn. 21 to the current versus time response and subsequent data treatment as described herein allowed for a reliable estimate of equilibrium value consistent with complete consumption of the glucose. Because this method estimated total glucose consumed, it provides an invaluable tool to examine decline in sensitivity of the response of the biographer glucose monitor to glucose over an extended period.

As is apparent to one of skill in the art, various modification and variations of the above embodiments can be made without departing from the spirit and scope of this invention. Such modifications and variations are within the scope of this invention.

What is claimed is

1. A method for measuring glucose present in a subject, said method comprising:
    (A) transdermally extracting a sample comprising glucose from the subject using a sampling system that is in operative contact with a skin or mucosal surface of said subject, the system including first and second iontophoresis electrodes such that current flows through the first electrode to a first conductive medium into the skin, and back out from the skin through a second conductive medium to the second electrode;
    (B) obtaining a measured signal over time, comprising a measured signal response curve, from the extracted glucose, wherein said measured signal is specifically related to the amount or concentration of glucose, and said measured signal response curve comprises kinetic and equilibrium regions;
    (C) using (i) a mathematical model comprising selected parameters, wherein said model describes the measured signal response curve, and said mathematical model is selected from the group consisting of a first order process, combined first order and zero order process, a parallel multiple first order process, a flux process, and an n.sup.th order process, and (ii) an error minimization method, to iteratively estimate values of the parameters using said model and error minimization method to fit a predicted response curve to said measured signal response curve, wherein (a) the error minimization method provides a calculated error based on differences between said predicted and measured signal response curves, and (b) said estimating is iteratively performed until the calculated error between the predicted and measured signal response curves falls within an acceptable range or until no further statistically significant change is seen in the calculated error, at which time iterative estimation of the parameters is stopped, said iterative estimation and error minimization results in a predicted response curve corresponding to said measured signal response curve, said predicted response curve yields a predicted end-point value and a measurement correlated to the amount or concentration of the glucose in the sample of the subject.

2. The method of claim 1, wherein said measured signal response curve comprises a measurement of current over time, or measurement of charge over time.

3. The method of claim 2, wherein said measured signal response curve comprises a measurement of current over time, said predicted end-point value is an estimated signal at equilibrium, where said predicted end-point value provides a predicted final background value, and said measurement correlated to the amount or concentration of glucose corresponds to an area under the predicted response curve.

4. The method of claim 3, wherein said area under the predicted response curve is obtained by integration of the predicted response curve.

5. The method of claim 4, wherein before said integration is performed said final background value is used to perform a background subtraction correction of the predicted response curve and said measurement correlated to the amount or concentration of glucose corresponds to an area under the predicted response curve.

6. The method of claim 4, wherein the end-point value of the integrated predicted response curve is converted to an amount or concentration of the glucose.

7. The method of claim 5, wherein the end-point value of the integrated predicted response curve is converted to an amount or concentration of the glucose.

8. The method of claim 1, wherein the mathematical model further comprises a zero-order component.

9. The method of claim 6, wherein conversion of the end-point value of the integrated predicted response curve to an amount or concentration of glucose is performed by a method comprising applying a calibration value.

10. The method of claim 1, wherein said mathematical model comprises more than one process and each process comprises selected parameters.

11. The method of claim 10, wherein each process has a corresponding weighting factor.

12. The method of claim 1, wherein a background subtraction is performed on the measured signal response curve before (C) is performed.

13. The method of claim 1, wherein (A), (B), and (C) are performed at least two times to obtain a series of measurements.

14. The method of claim 13, wherein after estimation of each predicted response curve for each measured signal response curve in the series of measurements an amount or concentration of the glucose is determined based on the predicted response curve.

15. The method of claim 1, wherein said measured signal response curve comprises data points.

16. The method of claim 15, wherein at least three data points are obtained from the kinetic region of the measured signal response curve, and these data points are used to estimate the half-life of the measured signal.

17. The method of claim 1, wherein said obtaining is carried out for a defined period of time.

18. The method of claim 1, wherein said mathematical model comprises a mathematical model selected from the group consisting of a first order process, combined first order and zero order process, a parallel multiple first order process, a flux process, and an n.sup.th order process.

19. The method of claim 1, wherein said transdermally extracting the sample is performed using a sampling method comprising a sampling method selected from the group consisting of iontophoresis, sonophoresis, microdialysis, suction, and passive diffusion.

* * * * *